(12) United States Patent
Chen et al.

(10) Patent No.: US 10,279,334 B2
(45) Date of Patent: May 7, 2019

(54) MICROPOROUS METAL-ORGANIC FRAMEWORKS FOR THE REMOVAL OF ACETYLENE FROM ETHYLENE

(71) Applicant: THE BOARD OF REGENTS OF THE UNIVERSITY OF TEXAS SYSTEM, Austin, TX (US)

(72) Inventors: Banglin Chen, San Antonio, TX (US); Tong-Liang Hu, Tianjin (CN)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/560,570

(22) PCT Filed: Mar. 23, 2016

(86) PCT No.: PCT/US2016/023765
§ 371 (c)(1),
(2) Date: Sep. 22, 2017

(87) PCT Pub. No.: WO2016/154300
PCT Pub. Date: Sep. 29, 2016

(65) Prior Publication Data
US 2018/0085733 A1    Mar. 29, 2018

Related U.S. Application Data

(60) Provisional application No. 62/137,561, filed on Mar. 24, 2015.

(51) Int. Cl.
| | | |
|---|---|---|
| *C07F 1/08* | (2006.01) | |
| *C07F 3/02* | (2006.01) | |
| *B01J 20/22* | (2006.01) | |
| *B01D 53/02* | (2006.01) | |
| *B01J 20/28* | (2006.01) | |
| *C07F 15/02* | (2006.01) | |
| *C07F 15/06* | (2006.01) | |
| *C07C 7/12* | (2006.01) | |

(52) U.S. Cl.
CPC ............ *B01J 20/226* (2013.01); *B01D 53/02* (2013.01); *B01J 20/28011* (2013.01); *B01J 20/28057* (2013.01); *B01J 20/28069* (2013.01); *C07C 7/12* (2013.01); *C07F 1/08* (2013.01); *C07F 3/02* (2013.01); *C07F 15/025* (2013.01); *C07F 15/065* (2013.01); *B01D 2253/204* (2013.01); *B01D 2256/24* (2013.01); *B01D 2257/7022* (2013.01)

(58) Field of Classification Search
None
See application file for complete search history.

(56) References Cited

U.S. PATENT DOCUMENTS

| | | | | |
|---|---|---|---|---|
| 2014/0205846 A1* | 7/2014 | McFarland | ........... | C07C 229/76 428/472.2 |
| 2015/0225438 A1* | 8/2015 | Johnson | .................. | A61K 47/22 514/188 |
| 2016/0159822 A1* | 6/2016 | Tan | ........................... | C07F 1/08 556/115 |
| 2017/0073364 A1* | 3/2017 | Dinca | .................... | B01J 20/226 |

FOREIGN PATENT DOCUMENTS

WO    WO 2014/130246    8/2014

OTHER PUBLICATIONS

Banerjee, "Porous Metal Organic Frameworks (MOFs) for Reversible Gas Storage and Sequestration Applications," *Proc. Indian Nat. Sci. Acad.*, 78(4):693-699, 2012.

Bloch et al., "Hydrocarbon separations in a metal-organic framework with open iron(II) coordination sites," *Science*, 335:1606-1610, 2012.

Burd et al., "Highly Selective Carbon Dioxide Uptake by [Cu (bpy-$n$)$_2$(SiF$_6$)] (bpy-1=4,4'-Bipyridine; bpy-2=1,2-Bis(4-pyridyl)ethene)," *J. Am. Chem. Soc.* 134, 3663-3666, 2012.

Chen et al., "A Microporous Metal-Organic Framework for Gas-Chromatographic Separation of Alkanes," *Angew. Chem. Int. Ed.* 45, 1390-1393, 2006.

Chen et al., "Metal-Organic Frameworks with Functional Pores for Recognition of Small Molecules," *Acc. Chem. Res.* 43, 1115-1124, 2010.

Farha et al., "De novo synthesis of a metal-organic framework material featuring ultrahigh surface area and gas storage capacities," *Nat. Chem.* 2, 944-948, 2010.

Férey et al., "Large breathing effects in three-dimensional porous hybrid matter: facts, analyses, rules and consequences," *Chem. Soc. Rev.*, 38, 1380, 2009.

(Continued)

*Primary Examiner* — Tam M Nguyen
(74) *Attorney, Agent, or Firm* — Parker Highlander PLLC

(57) ABSTRACT

A metal-organic framework (MOF) and uses thereof are provided herein, including MOF comprising a repeat unit of the formula [ML], wherein L is a ligand of the following formula: and M is a divalent metal such as copper. The MOFs provided herein may be used in the separation of two or more gaseous molecules from each other. In some embodiments, the gaseous molecules are ethylene and acetylene.

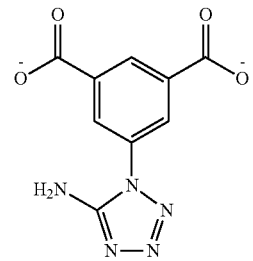

14 Claims, 10 Drawing Sheets

(56) References Cited

OTHER PUBLICATIONS

Furukawa et al., "The Chemistry and Application of Metal-Organic Frameworks," *Science*, 341:974, 2013.

Guo et al., "A Metal-Organic Framework with Optimized Open Metal Sites and Pore Spaces for High Methane Storage at Room Temperature," *Angew. Chem., Int. Ed, 50*, 3178. 2011.

He et al., "A series of metal-organic frameworks with high methane uptake and an empirical equation for predicting methane storage capacity," *Energy Environ. Sci., 6*, 2735, 2013.

He et al., "Microporous metal-organic frameworks for storage and separation of small hydrocarbons," *Chem. Commun., 48*, 11813, 2012.

International Search Report and Written Opinion issued in corresponding PCT Application No. PCT/US2016/23765, dated Jun. 17, 2016.

Li et al., "A Porous Metal-Organic Framework with Dynamic Pyrimidine Groups Exhibiting Record High Methane Storage Working Capacity," *J. Am. Chem. Soc.* 136, 6207-6210, 2014.

Li et al., "Enhanced Binding Affinity, Remarkable Selectivity, and High Capacity of $CO_2$ by Dual Functionalization of a *rht*-Type Metal-Organic Framework," *Angew. Chem. Int. Ed.* 51, 1412-1415; 2012.

Li et al., "Metal-Cation-Directed de Novo Assembly of a Functionalized Guest Molecule in the Nanospace of a Metal-Organic Framework," *J. Am. Chem. Soc.* 136, 1202-1205, 2014.

Li et al., "Porous materials with pre-designed single-molecule traps for $CO_2$ selective adsorption," *Nat. Commun.* 4, 1538, 2013.

Li et al., "Porous Metal-Organic Frameworks for Gas Storage and Separation: What, How, and Why?" *J. Phys. Chem. Lett.* 5, 3468-3479, 2014.

Li et al., "Selective gas adsorption and separation in metal-organic frameworks," *Chem. Soc. Rev.* 38, 1477-1504, 2009.

Lin et al., "Single-Walled Polytetrazolate Metal-Organic Channels with High Density of Open Nitrogen-Donor Sites and Gas Uptake," *J. Am. Chem. Soc.* 134, 784-787, 2012.

Ma et al., "Highly Porous and Robust 4,8-Connected Metal-Organic Frameworks for Hydrogen Storage," *J. Am. Chem. Soc.* 131, 4610-4612, 2009.

Ma et al., "Metal-Organic Framework from an Anthracene Derivative Containing Nanoscopic Cages Exhibiting High Methane Uptake," *J. Am. Chem. Soc., 130*, 1012, 2008.

Mohideen et al., "Protecting group and switchable pore-discriminating adsorption properties of a hydrophilic-hydrophobic metal-organic framework," *Nat. Chem.* 3, 304-310, 2011.

Motkuri et al., "Fluorocarbon adsorption in hierarchical porous frameworks," *Nat. Commun.* 5, 4368, 2014.

Nugent et al., "Porous materials with optimal adsorption thermodynamics and kinetics for $CO_2$ separation," *Nature* 495, 80-84, 2013.

Sato et al., "Self-accelerating CO sorption in a soft nanoporous crystal," *Science* 343, 167-170, 2014.

Shekhah et al., "Made-to-order metal-organic frameworks for trace carbon dioxide removal and air capture," *Nat. Commun.* 5, 4228, 2014.

Vaidhyanathan et al., "Direct observation and quantification of CO☐ binding within an amine-functionalized nanoporous solid," *Science* 330, 650-653, 2010.

Wen et al., "A microporous metal-organic framework with rare lvt topology for highly selective $C_2H_2/C_2H_4$ separation at room temperature ," *Chem. Commun.* 51:5610-5613, 2015.

Xiang et al., "Exceptionally high acetylene uptake in a microporous metal-organic framework with open metal sites," *J. Am. Chem. Soc.*, 131(34):12415-12419, 2009.

Xiang et al., "Microporous metal-organic framework with potential for carbon dioxide capture at ambient conditions," *Nat. Commun.* 3, 954; 2012.

Xiang et al., "Open Metal Sites within Isostructural Metal-Organic Frameworks for Differential Recognition of Acetylene and Extraordinarily High Acetylene Storage Capacity at Room Temperature," *Angew. Chem. Int. Ed.* 49, 4615-4618, 2010.

Xiang et al., "Rationally tuned micropores within enantiopure metal-organic frameworks for highly selective separation of acetylene and ethylene," *Nat. Commun.* 2, 204, 2011.

Yang et al., "Supramolecular binding and separation of hydrocarbons within a functionalized porous metal-organic framework," *Nat. Chem.* 7, 121-129, 2015.

Zhang and Chen, "Optimized Acetylene/Carbon Dioxide Sorption in a Dynamic Porous Crystal," *J. Am. Chem. Soc.* 131, 5516-5521, 2009.

Zhang et al., "Geometry analysis and systematic synthesis of highly porous isoreticular frameworks with a unique topology," *Nat. Commun.* 3, 642, 2012.

Zhang et al., "New Three-Dimensional Porous Metal Organic Framework with Tetrazole Functionalized Aromatic Carboxylic Acid: Synthesis, Structure, and Gas Adsorption Properties," *Inorg. Chem.*, 49(24):11581-11586, 2010.

Zhao et al., "Hysteretic adsorption and desorption of hydrogen by nanoporous metal-organic frameworks," *Science* 306, 1012-1015, 2004.

Zhao et al., "Selective anion exchange with nanogated isoreticular positive metal-organic frameworks," *Nat. Commun.* 4, 2344, 2013.

\* cited by examiner $S_{BET} = [1/(0.00471-0.00000138744)]/22414 \times 6.023 \times 10^{23} \times 0.170 \times 10^{-18} = 970 \text{ m}^2\text{g}^{-1}$.

$S_{Langmuir} = [(1/0.00416)/22414] \times 6.023 \times 10^{23} \times 0.170 \times 10^{-18} = 1098 \text{ m}^2\text{g}^{-1}$.

MICROPOROUS METAL-ORGANIC FRAMEWORKS FOR THE REMOVAL OF ACETYLENE FROM ETHYLENE

This application is a national phase application under 35 U.S.C. § 371 of International Application No. PCT/US2016/023765, filed Mar. 23, 2016, which claims the benefit of U.S. Provisional Application Ser. No. 62/137,561, filed on Mar. 24, 2015, the entire contents of which are incorporated herein by reference.

BACKGROUND OF THE INVENTION

I. Field of the Invention

The present disclosure relates generally to the fields of chemistry and materials science. More particularly, it concerns metal-organic frameworks, compositions thereof and methods use thereof, including for separating gas molecules such as ethylene and acetylene.

II. Description of Related Art

Microporous metal-organic frameworks (MOFs) have emerged as a new type of porous materials for gas storage, separation, sensing and heterogeneous catalysis. The tunable pores and the immobilized functional sites within such microporous MOFs have enabled them to direct specific recognition of certain molecules based upon size and functionality.

Ethylene is an industrially utilized raw chemical with over 100 million tons produced in 2006 (Sundaram et al., 1995). Ethylene is used to produce polymers and other useful chemicals (Sundaram et al., 1995). During the production of ethylene through the cracking of ethane, propane and heavier hydrocarbons, a small amount of acetylene as an impurity of about 1% was also generated. Acetylene in the ethylene feed should be reduced to an acceptable level because acetylene has a deleterious effect on end products of ethylene. For example, acetylene can poison catalysts during ethylene polymerization and thus affect the quality of the resulting polyethylene. Furthermore, acetylene can form solid metal acetylides, which can block the fluid stream and lead to explosion (Molero et al., 1999).

Extensive efforts have been pursued to remove acetylene from ethylene/acetylene mixtures (Studt, et al., 2008 and Lewis, 1974). In the petro-chemical industry, current commercial approaches include partial hydrogenation of acetylene into ethylene over a noble metal catalyst such as a supported Pd catalyst and solvent extraction of cracked olefins using an organic solvent such as DMF and acetone. Both of which have some drawbacks: the former process suffers from the need of noble-metal catalyst and the loss of olefins due to the over hydrogenation to paraffins, while the latter wastes much amount of solvents. Porous materials through selective adsorption separation of acetylene over ethylene might provide the alternative cost and energy efficient approach for this industrially useful but difficult task, including removing acetylene from ethylene in amounts as low as 1%.

Among diverse porous materials, the emerging microporous metal-organic frameworks (MOFs) are useful in gas separations including the removal of acetylene from ethylene/acetylene mixtures. The pores within microporous MOFs can be tuned to enforce their size selective sieving effects while their pore surfaces can be readily functionalized to induce their preferential interactions with specific gas molecules (Furukawa, et al., 2013; Sato, et al., 2014; Zhao, et al., 2013; An, et al., 2012; Xiang, et al., 2012; Li, et al., 2013; Vaidhyanathan, et al., 2010; Chen, et al., 2010; Lin et al., 2012; Férey, et al., 2005; Zhao, et al., 2004; Farha, et al., 2010; Mohideen, et al., 2011; Zhang, et al., 2012; Zhang & Chen, 2009; Li, et al., 2012; Burd, et al., 2012; Nugent, et al., 2013; Shekhah, et al., 2014; Li, et al., 2014; Ma, et al., 2009, Lan, et al., 2011; Motkuri, et al., 2014; Li., et al., 2014; Li, et al., 2014; Chen, et al., 2006; Guo, et al., 2011 and He, et al., 2012). MOFs for the separation of $C_2H_2/C_2H_4$ have not been fully explored. An initial microporous MOF for this separation was developed in 2011 (Xiang, et al., 2011). The micropores have been further developed through the interplay of metalloligands and organic linkers, and thus to optimize the separation selectivities. Although the separation selectivities of these MOFs for the separation of $C_2H_2/C_2H_4$ are high because of their high sieving effects; their narrow pores have also limited their acetylene uptakes, which eventually affect their overall performance for separation of $C_2H_2/C_2H_4$, as clearly demonstrated in the simulated breakthrough curves (Das, et al., 2012). Further development led to the discovery of MOF-74 series for $C_2H_2/C_2H_4$ separations (Bloch, et al., 2012 and He, et al., 2012). This series of MOFs have high densities of open metal sites which can enforce their acetylene uptakes (Xiang, et al., 2009 and Xiang, et al., 2010), but their pores are too large to introduce size sieving effects. Furthermore, the open metal sites have strong interactions with ethylene molecules as well, so MOF-74 series have systematically low selectivities for $C_2H_2/C_2H_4$ separation. The MOFs for $C_2H_2/C_2H_4$ separation are those with high $C_2H_2/C_2H_4$ sieving effects but without sacrificing acetylene uptakes. There has been some progress on microporous MOFs for $C_2H_2/C_2H_4$ separation; however, their pore structures still cannot meet the necessary selectivity criteria and their separation performances are comparable to earlier MOFs (Yang, et al., 2015 and Wen, et al., 2015). As such MOFs that exhibit selective and effective removal of acetylene from ethylene/acetylene mixtures containing mixtures containing as little as 1% acetylene are needed.

SUMMARY OF THE INVENION

In some aspects, the present disclosure provides MOFs which may be used to remove acetylene from an acetylene/ethylene mixture. In some aspects, the present invention provides metal-organic frameworks comprising a repeat unit of the formula [ML], wherein L is a ligand of the formula:

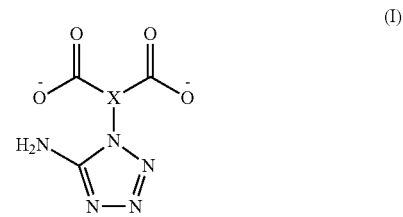

wherein:

X is an arenetriyl$_{(C \leq 12)}$, a heteroarenetriyl$_{(C \leq 12)}$, or a substituted version of either of these groups; and M is a divalent transition metal cation. In some embodiments, M is divalent copper ion. In some embodiments, L is a ligand of the formula:

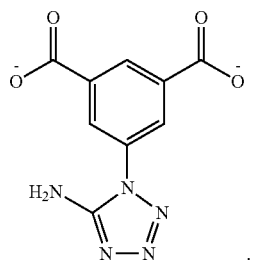 [SMILES: Nc1nnnn1-c1cc(C(=O)O)cc(C(=O)O)c1]

In some embodiments, the MOF is activated for sorption of gas molecules.

In some embodiments, the MOF further comprises one or more than one type of guest molecule. In some embodiments, one type of guest molecule is a solvent molecule. In some embodiments, the solvent molecule is water. In other embodiments, the solvent molecule is N,N'-dimethylformamide. In other embodiments, the solvent molecule is methanol. In other embodiments, the solvent molecule is acetone. In some embodiments, the solvent molecules occupy the pores of the MOF.

In other embodiments, one type of guest molecule is a gas molecule. In some embodiments, the gas molecule is an alkyne$_{(C \leq 8)}$. In some embodiments, the gas molecule is acetylene. In other embodiments, the gas molecule is an alkene$_{(C \leq 8)}$. In some embodiments, the gas molecule is ethylene. In other embodiments, the gas molecule is a mixture of acetylene and ethylene. In some embodiments, the MOF is substantially free from any solvent molecules.

In some embodiments, the MOF has a weight percentage at least 90% attributable to repeat units of the formula [ML]. In some embodiments, the MOF has a weight percentage at least 95% attributable to repeat units of the formula [ML]. In some embodiments, the MOF has a weight percentage at least 99% attributable to repeat units of the formula [ML]. In some embodiments, the MOF has been adhered to a fixed surface.

In yet another aspect, the present invention provides methods of separating two or more compounds using an MOF comprising:
(a) obtaining a MOF of the present invention;
(b) combining the MOF with a mixture comprising a first compound and one or more second compounds; and
(c) separating the first compound from the one or more second compounds based on their differential sorption rate within the MOF.

In some embodiments, the compounds are gas molecules. In some embodiments, the first compound is an alkyne$_{(C \leq 8)}$. In some embodiments, the first compound is acetylene. In some embodiments, the second compound is an alkene$_{(C \leq 8)}$. In some embodiments, the second compound is ethylene. In some embodiments, the mixture comprises from about 1:999 to about 1:1 of the first compound to the second compound. In some embodiments, the mixture comprises about 1:99 the first compound to the second compound.

In some embodiments, the separation is carried out at a pressure of about 100 kPa. In some embodiments, the MOF is adhered to a fixed bed surface. In some embodiments, an absorber is packed with the MOF. In some embodiments, the absorption is carried out at a temperature from about 0° C. to about 75° C. In some embodiments, the absorption is carried out at about room temperature.

In still another aspect, the present invention provides methods of using an MOF in an application selected from sensing, heterogeneous catalysis, drug delivery, lithium sulfide battery, membranes, and analytical devices.

In yet another aspect, the present invention provides metal-organic frameworks (MOFs) comprising a repeat unit of the formula [CuL], wherein L is a ligand of the formula:

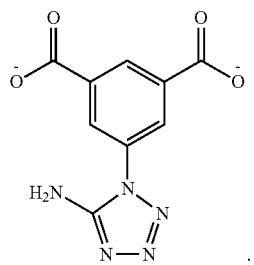

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

(FIG. 5A) The coordination environment of organic ligand ATBDC$^{2-}$ and Cu(II), and dinuclear copper(II) unit as a 6-connected node (dark balls) and ATBDC$^{2-}$ as a 3-connected node (light ball). (FIG. 5B) The framework topology of apo-type (3,6)-connected network with Schläfli symbol $\{4.6^2\}_2\{4^2.6^9.8^4\}$. (FIG. 5C) The 3D structure viewed along the c axis showing the 1D rhombic channels of about 4.3 Å in diameter. (FIG. 5D) The cage with the diameter of about 4.0 Å between 1D channels with window openings of 3.3 Å. Solvent molecules were omitted for the clarity.

(FIG. 6B) Plot of the term $Q(1-P/P_0)$ vs $P/P_0$. (FIG. 6C) The BET and Langmuir (FIG. 6D) surface areas of UTSA-100a obtained from the $N_2$ adsorption isotherm at 77 K.

(FIG. 10A) $C_2H_2/C_2H_4$ adsorption selectivity, and (FIG. 10C) uptake capacity of $C_2H_2$ for adsorption from $C_2H_2/C_2H_4$ mixture containing 1% $C_2H_2$. The total bulk gas phase is at 296 K and 100 kPa. The partial pressures of $C_2H_2$ and $C_2H_4$ are, respectively, p1=1 kPa, p2=99 kPa. (FIG. 10B) IAST calculations of the $C_2H_2/C_2H_4$ adsorption selectivity for FeMOF-74, NOTT-300, and UTSA-100a as a function of the mole fraction of $C_2H_2$ in the gas phase. The total gas pressure is constant at 100 kPa. Note: The data for FeMOF-74 is at the temperature of 318 K; this is the lowest temperature used in the isotherm measurements of Bloch et al. (Bloch, et al., 2012). The data for NOTT-300 is at 293 K. M'MOF-3a, MgMOF-74, CoMOF-74, FeMOF-74, NOTT-300, and UTSA-100a.

(FIG. 11A) Transient breakthrough curve of $C_2H_2/C_2H_4$ mixture in an adsorber bed packed with UTSA-100a. The partial pressures of $C_2H_2$, and $C_2H_4$ in the inlet feed gas mixture are, respectively, $p_1=1$ kPa, $p_2=99$ kPa. For the breakthrough simulations, the following parameter values were used, L=0.12 m; ε=0.75; u=0.00225 m/s. (FIG. 11B) Ppm $C_2H_2$ in the outlet gas of an adsorber bed packed with UTSA-100a and various MOFs. M'MOF-3a, MgMOF-74, CoMOF-74, FeMOF-74, NOTT-300, and UTSA-100a. (FIG. 11C) Plot of $C_2H_2$ captured per L of adsorbent (<40 ppm $C_2H_2$ in outlet gas), during the time interval $0-\tau_{break}$, plotted as a function of the time interval $\tau_{break}$. (FIG. 11D) Experimental column breakthrough curve for $C_2H_2/C_2H_4$ mixed gas containing 1% $C_2H_2$ over UTSA-100a. Note: The temperatures are 318 K and 293 K for FeMOF-74 and NOTT-300, respectively.

(FIG. 12A) The pore structure showing the zigzag channels along the c axis and the cages with the diameter of about 4.0 Å in the pore wall with the window openings of 3.3 Å. (FIG. 12B) The acetylene sits right at the small cage connecting two adjacent channel pores. (multiple-point interactions of the acetylene molecule with framework: d [O(—$CO_2$) . . . H($C_2H_2$)]=2.252 Å, d [H(—$NH_2$) . . . ($C_2H_2$)]=2.856 Å). (FIG. 12C) Pore size distribution (PSD) of UTSA-100a. PSD was calculated using the well-known method by Bhattacharya & Gubbins (2006). The van der Waals diameters of the framework atoms were adopted from the Cambridge Crystallographic Center. (FIG. 12D) Pore size variation along the pore channel (in c axis direction), within the crystal unit cell of UTSA-100a.

DESCRIPTION OF ILLUSTRATIVE EMBODIMENTS

I. Definitions

Figure 1:
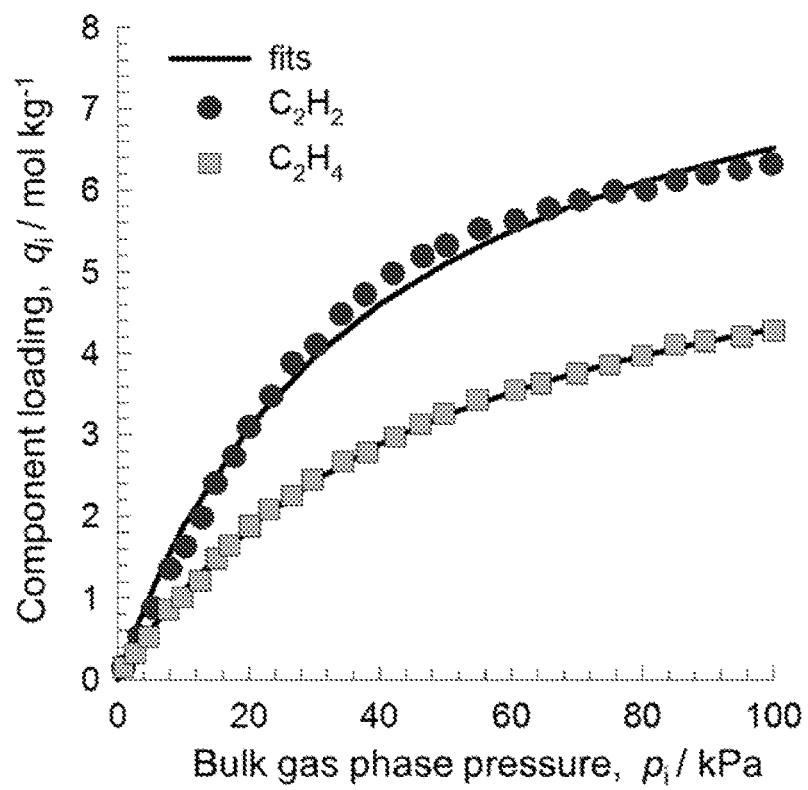
FIG. 1 shows the comparison of component loadings for $C_2H_2$ (circles) and $C_2H_4$ (squares) at 293 K in NOTT-300 with 1-site Langmuir isotherm fits.

"Metal-organic frameworks" (MOFs) are framework materials, typically three-dimensional, self-assembled by the coordination of metal ions with organic linkers exhibiting porosity, typically established by gas adsorption. The MOFs discussed and disclosed herein are at times simply identified by their repeat unit as defined below without brackets or the subscript n. A mixed-metal-organic frameworks (M'MOF) is a subset of MOFs having two of more types of metal ions.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$—, the repeat unit is —$CH_2CH_2$—. The subscript "n" denotes the degree of polymerisation, that is, the number of repeat units linked together. When the value for "n" is left undefined, it simply designates repetition of the formula within the brackets as well as the polymeric and/or framework nature of the material. The concept of a repeat unit applies equally to where the connectivity between the repeat units extends into three dimensions, such as in metal organic frameworks, cross-linked polymers, thermosetting polymers, etc. Note that for MOFs the repeat unit may also be shown without the subscript n.

"Pores" or "micropores" in the context of metal-organic frameworks are defined as open space within the MOFs; pores become available, when the MOF is activated for the storage of gas molecules. Activation can be achieved by heating, e.g., to remove solvent molecules.

"Multimodal size distribution" is defined as pore size distribution in three dimensions.

"Multidentate organic linker" is defined as ligand having several binding sites for the coordination to one or more metal ions.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —$C_6H_4CH_2CH_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

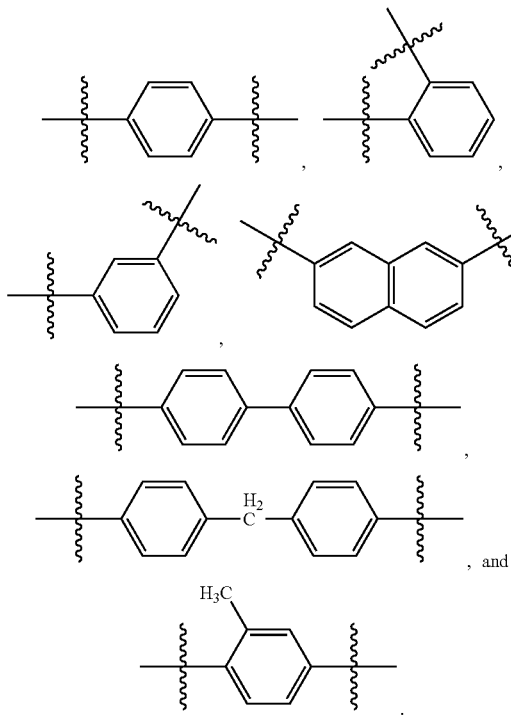

The term "arenetriyl" when used without the "substituted" modifier refers to a trivalent aromatic group with three aromatic carbon atoms as points of attachment, said carbon atoms forming part of one or more six-membered aromatic ring structure(s) wherein the ring atoms are all carbon, and wherein the trivalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring if present. If more than one ring is present, the rings may be fused or unfused. Unfused rings may be connected via one or more of the following: a covalent bond, alkanediyl, or alkenediyl groups (carbon number limitation permitting). Non-limiting examples of arenetriyl groups include:

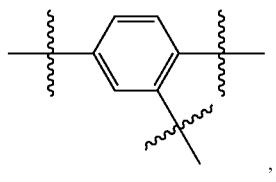

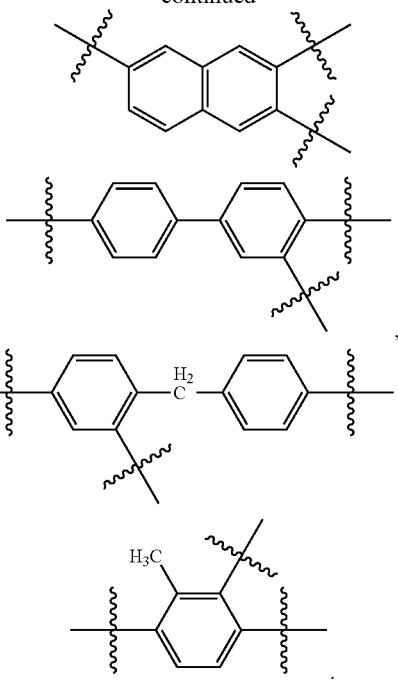

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

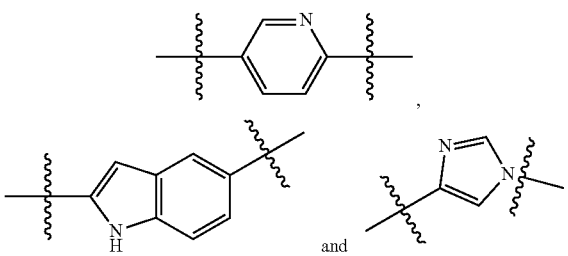

The term "heteroarenetriyl" when used without the "substituted" modifier refers to an trivalent aromatic group, with three aromatic carbon atoms, three aromatic nitrogen atoms, two aromatic carbon atom and one aromatic nitrogen atom, or one aromatic carbon atom and two aromatic nitrogen atom as the three points of attachment, said atoms forming part of one or more aromatic ring structure(s) wherein at least one of the ring atoms is nitrogen, oxygen or sulfur, and wherein the trivalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenetriyl groups include:

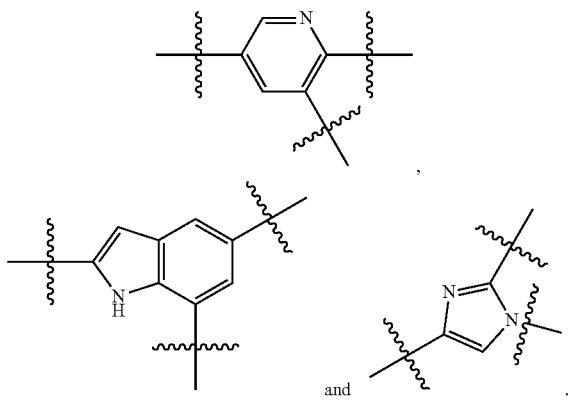

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include ¹³C and ¹⁴C. Additionally, it is contemplated that one or more of the metal atoms may be replaced by another isotope of that metal. In some embodiments, the copper atoms can be ⁶³Cu or ⁶⁵Cu. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Any undefined valency on a carbon atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

The term "saturated" when referring to an atom means that the atom is connected to other atoms only by means of single bonds.

The above definitions supersede any conflicting definition in any of the reference that is incorporated herein by reference. The fact that certain terms are defined, however, should not be considered as indicative that any term that is undefined is indefinite. Rather, all terms used are believed to describe the invention in terms such that one of ordinary skill can appreciate the scope and practice the present invention.

EXAMPLE 1

Methods and Materials

1. General Procedures and Materials.

Commercially available reagents were purchased in high purity and used without further purification. 5-(5-Amino-1H-tetrazol-1-yl)-1,3-benzenedicarboxylic acid (H₂ATBDC) was synthesized as described in the literature (Voitekhovich et al., 2005) and is shown in Scheme 1. ¹H NMR and ¹³C NMR spectra were obtained using a Varian INOVA 500 MHz spectrometer at room temperature. FTIR spectra were performed on a Bruker Vector 22 spectrometer at room temperature. Thermal gravimetric analysis (TGA) was performed under a nitrogen atmosphere with a heating rate of 3° C./min using a Shimadzu TGA-50 thermogravimetric analyzer. Powder X-ray diffraction (PXRD) patterns were measured by a Rigaku Ultima IV diffractometer operated at 40 kV and 44 mA with a scan rate of 1.0 deg min⁻¹.

Scheme 1: Synthetic Routes to the Organic Ligand H$_2$ATBDC

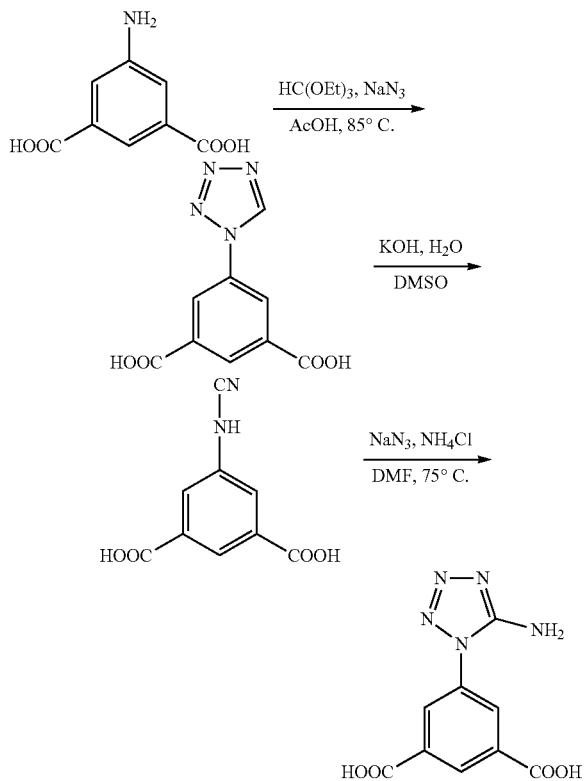

2. Gas Sorption Studies

A Micromeritics ASAP 2020 surface area analyzer was used to measure gas adsorption isotherms. To remove all the guest solvents in the framework, the fresh sample of UTSA-100 was guest-exchanged with dry acetone at least 10 times, filtered and degassed at room temperature (296 K) for one day, and then at 358 K for another 3 days until the outgas rate was 5 μmHg min$^{-1}$ prior to measurements. A sample of activated UTSA-100a (100-150 mg) was used for the sorption measurement and was maintained at 77 K with liquid nitrogen, at 273 K with an ice-water bath. As the center-controlled air conditioner was set up at 296 K, a water bath was used for adsorption isotherms at 296 K.

3. Fitting of Pare Component Isotherms

Experimental data on pure component isotherms for acetylene and ethylene in UTSA-100a were measured at temperatures of 273 and 296 K. The pure component isotherm data for acetylene and ethylene were fitted with the dual-Langmuir-Freundlich isotherm model $$q = q_{A,sat}\frac{b_A p^{v_A}}{1 + b_A p^{v_A}} + q_{B,sat}\frac{b_B p^{v_B}}{1 + b_B p^{v_B}}$$

with T-dependent parameters $b_A$, and $b_B$ $$b_A = b_{A0}\exp\left(\frac{E_A}{RT}\right);$$
$$b_B = b_{B0}\exp\left(\frac{E_B}{RT}\right)$$

The fitted parameter values are presented in Table 1.

TABLE 1

Dual-Langmuir-Freundlich parameter fits for UTSA-100a

| | Site A | | | | Site B | | | |
|---|---|---|---|---|---|---|---|---|
| | $q_{A,sat}$ mol kg$^{-1}$ | $b_{A0}$ Pa$^{-v}{}_i$ | $E_A$ kJ mol$^{-1}$ | $v_A$ dimensionless | $q_{B,sat}$ mol kg$^{-1}$ | $b_{B0}$ Pa$^{-v}{}_i$ | $E_B$ kJ mol$^{-1}$ | $v_B$ Dimensionless |
| C$_2$H$_2$ | 2 | 1.19 × 10$^{-9}$ | 26.5 | 1.25 | 15 | 2.42 × 10$^{-6}$ | 12.3 | 0.54 |
| C$_2$H$_4$ | 1.8 | 7.19 × 10$^{-12}$ | 33 | 1 | 1.15 | 3.37 × 10$^{-10}$ | 33 | 1 |

For FeMOF-74, the dual-site Langmuir-Freundlich parameters are from Bloch, et al. (2012). For convenience, the parameters are summarized in Table 2. For NOTT-300, the isotherm data at 293 K were fitted with a single-site Langmuir isotherm model; the fit parameters are specified in Table 3. FIG. 1 presents a comparison of component loadings for acetylene and ethylene at 293 K in NOTT-300 with 1-site Langmuir isotherm fits. The Langmuir fits are of good accuracy. For all other MOFs, the isotherm data are from He, et al. (2012).

TABLE 2

Dual-Langmuir-Freundlich parameter fits for FeMOF-74. The fit parameters are for 318 K from the paper by Bloch, et al. (2012).

| | Site A | | | Site B | | |
|---|---|---|---|---|---|---|
| | $q_{i,A,sat}$ mol kg$^{-1}$ | $b_{i,A}$ Pa$^{-v}{}_i$ | $v_{i,A}$ dimensionless | $q_{i,B,sat}$ mol kg$^{-1}$ | $b_{i,B}$ Pa$^{-v}{}_i$ | $v_B$ dimensionless |
| C$_2$H$_2$ | 5.3 | 1.086 × 10$^{-3}$ | 1 | 3.6 | 8.69 × 10$^{-6}$ | 1 |
| C$_2$H$_4$ | 3.6 | 3.71 × 10$^{-4}$ | 1.1 | 3.3 | 8.29 × 10$^{-5}$ | 1 |

TABLE 3

Single-site Langmuir fits for NOTT-300 at 293 K. The
isotherm data from Yang, et al. (2015) at 293 K are fitted.

| | $q_{A,sat}$ mol kg$^{-1}$ | $b_{A0}$ Pa$^{-1}$ |
|---|---|---|
| $C_2H_2$ | 9 | $2.62 \times 10^{-5}$ |
| $C_2H_4$ | 6.4 | $2.06 \times 10^{-5}$ |

4. Transient Breakthrough of Acetylene/Ethylene Mixtures in Fixed Bed Adsorbers:

The performance of industrial fixed bed adsorbers is dictated by a combination of adsorption selectivity and uptake capacity. For a proper comparison of various MOFs, transient breakthrough simulations using the simulation methodology described in the literature (Krishna & Long, 2011; Krishna, 2014, and Krishna, 2015) were performed. For the breakthrough simulations, the following parameter values were used: framework density, ρ (1146 kg m$^{-3}$), length of packed bed, L (0.12 m); voidage of packed bed, ε (0.75); superficial gas velocity at inlet, u (0.00225 m/s). For breakthrough simulations with NOTT-300, the framework density from the crystal structure information provided in the paper of Yang et al. (Yang, et al., 2015) were calculated and the resultant value was ρ (1062 kg m$^{-3}$). The framework densities for all other MOFs are available in the papers by Bloch, et al. (2012) and He, et al. (2012). The transient breakthrough simulation results are presented in terms of a dimensionless time, τ, defined by dividing the actual time, t, by the characteristic time, $$\frac{L\varepsilon}{u}.$$

5. Column Breakthrough Tests

Figure 2:
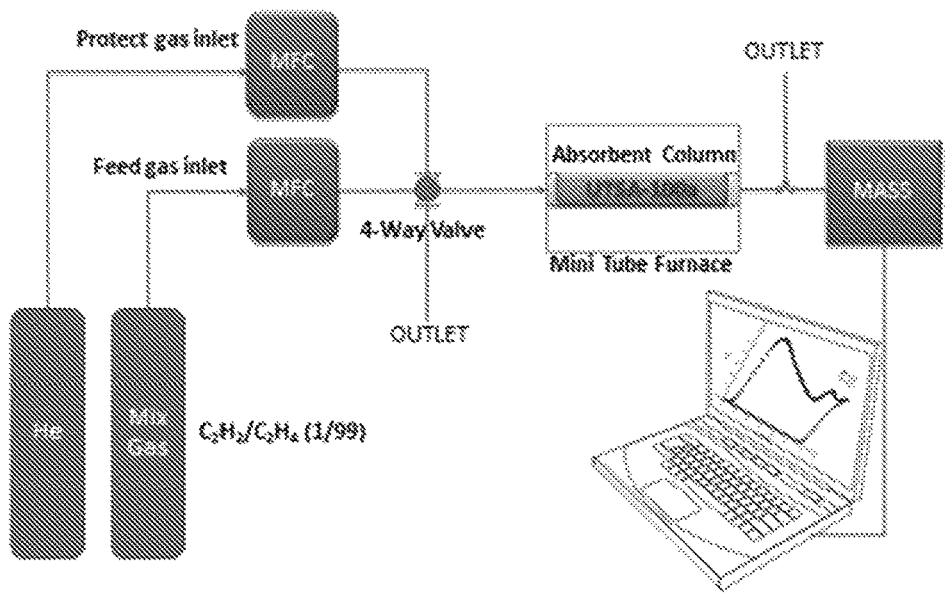
FIG. 2 shows a schematic illustration of the apparatus used for the breakthrough experiments.

The experimental set-up used for dynamic breakthrough measurements is shown in FIG. 2. The mixed-gas breakthrough separation experiment was conducted at 296 K using a lab-scale fix-bed reactor. In a typical experiment, 1.01 g of acetone-exchanged UTSA-100 powder was packed into a quartz column (5.8 mm I.D.×150 mm) with silica wool filling the void space. The sorbent was activated in situ in the column. A helium flow (5 ml/min) was used introduced after the activation process to purge the adsorbent. The flow of He was then turned off while a gas mixture of acetylene/ethylene (1:99, v/v) at 2 ml/min was allowed to flow into the column. The effluent from the column was monitored using a mass spectrometer (MS).

6. Single-crystal X-ray Crystallography

The crystal data were collected on an Agilent Supernova CCD diffractometer equipped with a graphite-monochromatic enhanced Cu Kα radiation (λ=1.54184 Å) at 100K. The datasets were corrected by empirical absorption correction using spherical harmonics, implemented in the SCALE3 ABSPACK scaling algorithm. The structure was solved by direct methods and refined by full matrix least-squares methods with the SHELX-97 program package (Sheldrick, 1997). The solvent molecules in the compound are highly disordered. The SQUEEZE subroutine of the PLATON software suit was used to remove the scattering from the highly disordered guest molecules (Spek, 1999 and Spek, 2003). The resulting new files were used to further refine the structures. The H atoms on C and N atoms were generated geometrically.

EXAMPLE 2

Synthetic Methods

Figure 3:
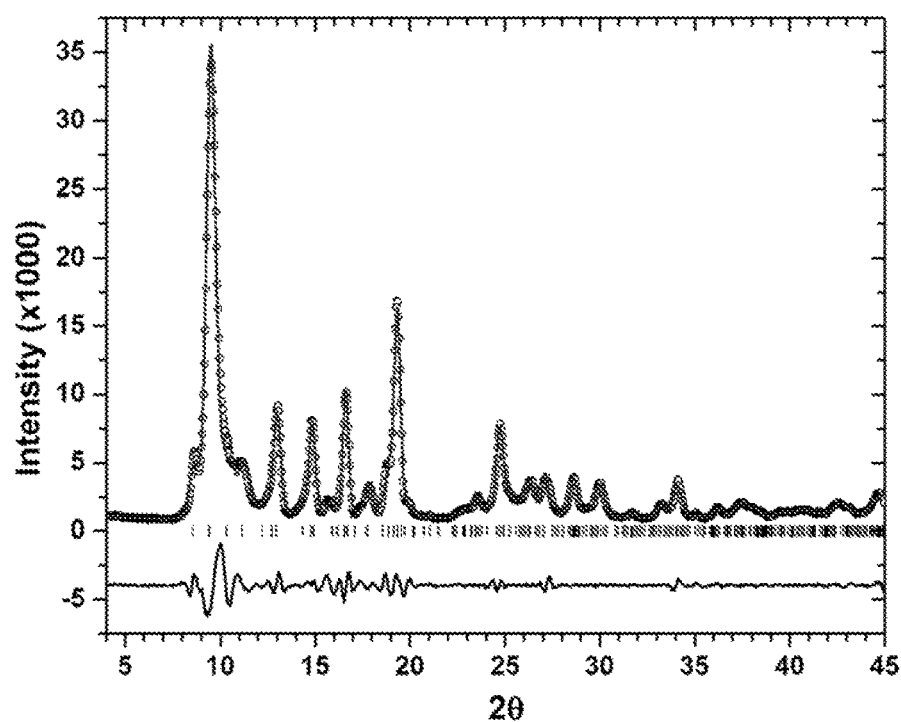
FIG. 3 shows experimental (circles), Le Bail fitted (line), and difference (line below observed and calculated patterns) PXRD profile for as-synthesized UTSA-100 at 298 K (Cu Ka radiation). Vertical bars indicate the calculated positions of Bragg peaks. Refined lattice parameters: a=12.369(3) Å, b=14.509(3) Å and c=20.755(6) Å. Goodness of fit: Rp=0.0677, Rwp=0.0871.
Figure 4:
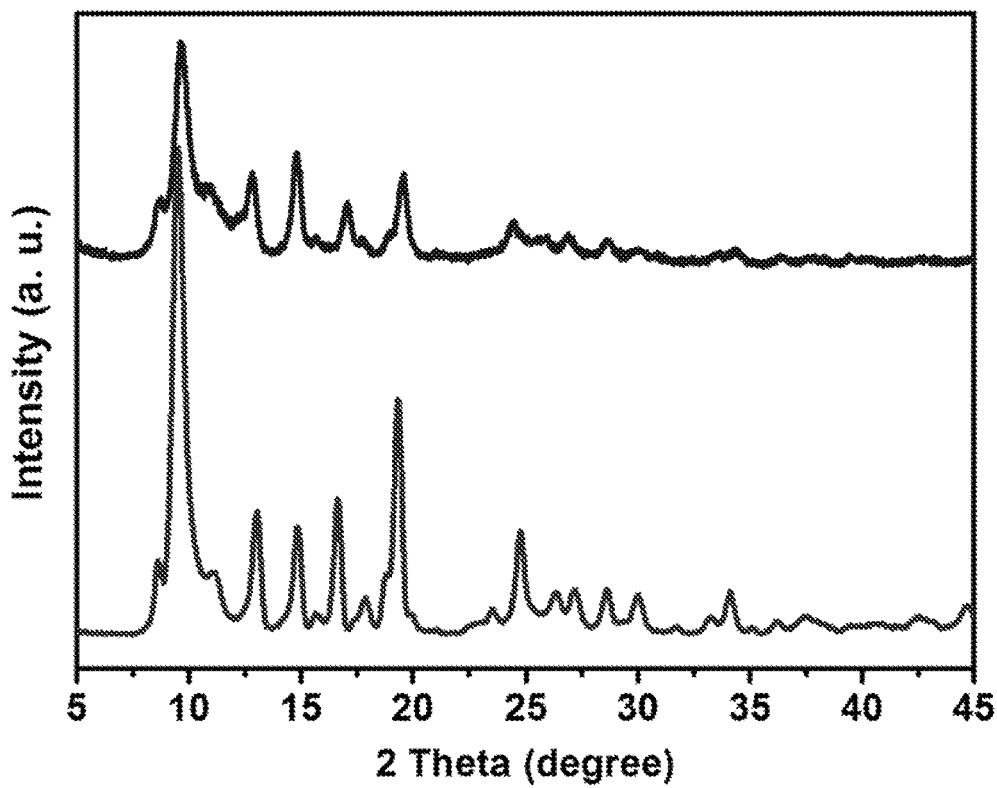
FIG. 4 shows the powder X-ray diffraction (PXRD) patterns of as-synthesized UTSA-100 (bottom) and activated UTSA-100a (top).

The new amino derivative of tetrazol-1,3-benzenedicarboxylic acid (5-(5-Amino-1H-tetra-zol-1-yl)-1,3-benzenedicarboxylic acid, $H_2$ATBDC) was prepared based on alkaline decomposition of the tetrazole ring and heterocyclization of the resulting N-arylcyanamides on interaction with ammonium azide generated in situ. Reaction of $CuCl_2 \cdot 2H_2O$ with $H_2$ATBDC in the solvothermal condition at 353 K formed UTSA-100 as green block single-crystals. It was formulated as [Cu(ATBDC)]·G (UTSA-100) by single-crystal X-ray diffraction (SXRD) studies, and the phase purity of the bulk material was independently confirmed by powder XRD (PXRD) (FIGS. 3 and 4). The desolvated [Cu(ATBDC)] (UTSA-100a) for the adsorption studies was prepared from the acetone-exchanged samples followed by the activation under ultrahigh vacuum at room temperature (296 K) for one day, and then at 358K for another 3 days. The PXRD profile of desolvated UTSA-100a indicates that it maintains the crystalline framework structure (FIG. 4).

Figures 5A, 5B, 5C, 5D:
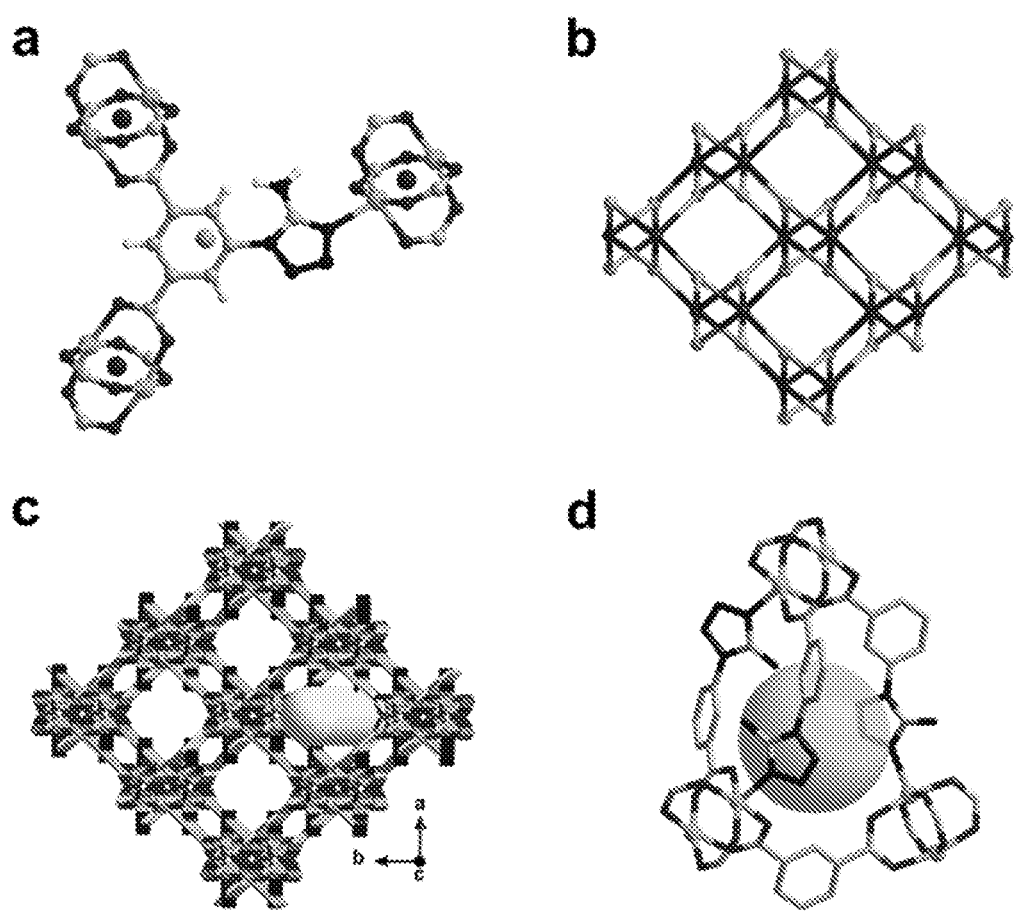
FIGS. 5A-5D show X-ray crystal structure of UTSA-100.

X-ray single-crystal structures reveal that UTSA-100 has a three-dimensional framework with rhombic open zigzag nano-channels with amino and tetrazole functionalized wall running in the c-direction (FIG. 5A-5D). There are 6-connected binuclear $Cu_2(COO)4$ units, which are bridged by 3-connected ATBDC$^{2-}$ anions to form a (3,6)-connected apo-type network with Schläfli symbol $\{4.6^2\}_2\{4^2.6^9.8^4\}$ (FIG. 5B). The 1D open zigzag channels with a diameter of about 4.3 Å are filled with the disordered solvent molecules (DMF and $CH_3OH$), and there are small cages with the diameter of about 4.0 Å between the 1D channels with window openings of 3.3 Å (FIG. 5D). The calculated solvent accessible volume of UTSA-100a is 51.0%, estimated using the PLATON program (Spek, 2001). The crystal structure data is shown in Table 4.

TABLE 4

Crystallographic data and structure refinement results
for UTSA-100 (from single-crystal X-ray diffraction
analysis on the as-synthesized sample).

| | UTSA-100 |
|---|---|
| Formula | $C_9H_5CuN_5O_4$ |
| Formula weight | 310.72 |
| Temperature/K | 100.33(10) |
| Crystal system | Orthorhombic |
| Space group | Pbcn |
| a (Å) | 12.1905(11) |
| b (Å) | 14.4177(13) |
| c (Å) | 20.4894(19) |
| α (°) | 90.00 |
| β (°) | 90.00 |
| γ (°) | 90.00 |
| V (Å$^3$) | 3601.2(6) |
| Z | 8 |
| $D_{calcd}$ (g cm$_{-3}$) | 1.146 |
| μ (mm$_{-1}$) | 1.858 |
| F (000) | 1240 |
| Crystal size/mm$^3$ | 0.15 × 0.10 × 0.08 |
| GOF | 0.961 |
| $R_{int}$ | 0.1589 |
| $R_1$, $wR_2$ [I >= 2σ (I)] | 0.0871, 0.2303 |
| $R_1$, $wR_2$ [all data] | 0.1106, 0.2569 |
| Largest diff. peak and hole (e Å$^{-3}$) | 2.187, −0.822 |

1. Synthesis of 5-(1H-tetrazol-1-yl)-3-benzenedicarboxylic acid

Glacial acetic acid (10.0 ml) was added with stirring to a suspension of 5-aminoisophthalic acid (4.54 g, 0.025 mol), and sodium azide (1.79 g, 0.0275 mol) in triethyl orthoformate (14.2 mL, 0.075 mol), and the mixture was stirred at 80-90° C. for 6 h. The reaction mixture was cooled, and concentrated hydrochloric acid (4.2 mL, 0.05 mol) and water (12.5 mL) were added. The precipitated solid was separated by filtration, washed with water, and dried. The obtained raw product was recrystallized from DMF. Yield: 82% (4.79 g). $^1$H NMR (500 MHz, DMSO-d$_6$, ppm): δ 13.78 (s, 2H, —CO$_2$H), 10.33 (s, 1H, —N$_4$CH), 8.65 (s, 2H, —C$_6$H$_3$), 8.55 (s, 1H, —C$_6$H$_3$).

2. Synthesis of 5-(Cyanoamino)-1,3-benzenedicarboxylic acid

DMSO (20.0 ml) was added dropwise with constant stirring to a suspension of 5-(1H-tetrazol-1-yl)-1,3-benzenedicarboxylic acid (4.68 g, 0.02 mol) in 22% aqueous KOH solution (12.0 mL). Gas evolution was observed, accompanied by self-heating of the reaction mixture. Stirring of the reaction mixture was continued for 2 days. The mixture was then diluted to 160 ml with water, acidified with concentrated hydrochloric acid to pH 3-4 and stored at 5-10° C. until precipitation of solid. The obtained product was filtered off, and dried in vacuum. Another portion of product was reprecipitated from the filtrate through salting out method using sodium salt. Yield: 93% (3.83 g). $^1$H NMR (500 MHz, DMSO-d$_6$, ppm): δ=7.67 (s, 1H, —C$_6$H$_3$), 7.40 (s, 2H, —C$_6$H$_3$).

3. Synthesis of 5-(5-Amino-1H-tetrazol-1-yl)-1,3-benzenedicarboxylic acid (H$_2$ATBDC)

A suspension of 5-(cyanoamino)-1,3-benzenedicarboxylic acid (2.06 g, 0.01 mol), sodium azide (0.98 g, 0.015 mol), and ammonium chloride (1.07 g, 0.02 mol) in DMF (25 mL) was stirred at 70-80° C. for 6 h, after which water (100 mL) was added to the reaction mixture. The white solid was precipitated through salting out method using sodium salt. The obtained product was filtered off, and dried in vacuum. Yield: 82% (2.04 g). $^1$H NMR (500 MHz, D$_2$O, ppm): δ=8.47 (s, 1H, —C$_6$H$_3$), 8.14 (s, 2H, —C$_6$H$_3$). $^{13}$C NMR (D$_2$O, ppm): δ=173.00, 138.49, 132.35, 130.43, 126.94.

4. Synthesis of UTSA-100

A mixture of CuCl$_2$.2H$_2$O (34 mg, 0.2 mmol) and the organic linker H$_2$ATBDC (50 mg, 0.2 mmol) was dispersed into an 8 mL mixed solvent (DMF/MeOH, 5/3, v/v) in a screw-capped vial (20 mL). And 5 drops of HBF$_4$ (48% w/w aqueous solution) was added. The suspension was sonicated until homogenous. The vial was capped and heated in an oven at 80° C. for 24 h. Green block crystals were obtained by filtration and washed with DMF several times to afford UTSA-100. IR (neat, cm$^{-1}$): 1739w, 1630s, 1596m, 1490w, 1457m, 1377s, 1255m, 1128w, 1097m, 1062w, 908m, 780m, 725s, 677m, 661m.

EXAMPLE 3

Results

1. Microporous Nature of UTSA-100

Figures 6A, 6B, 6C, 6D:
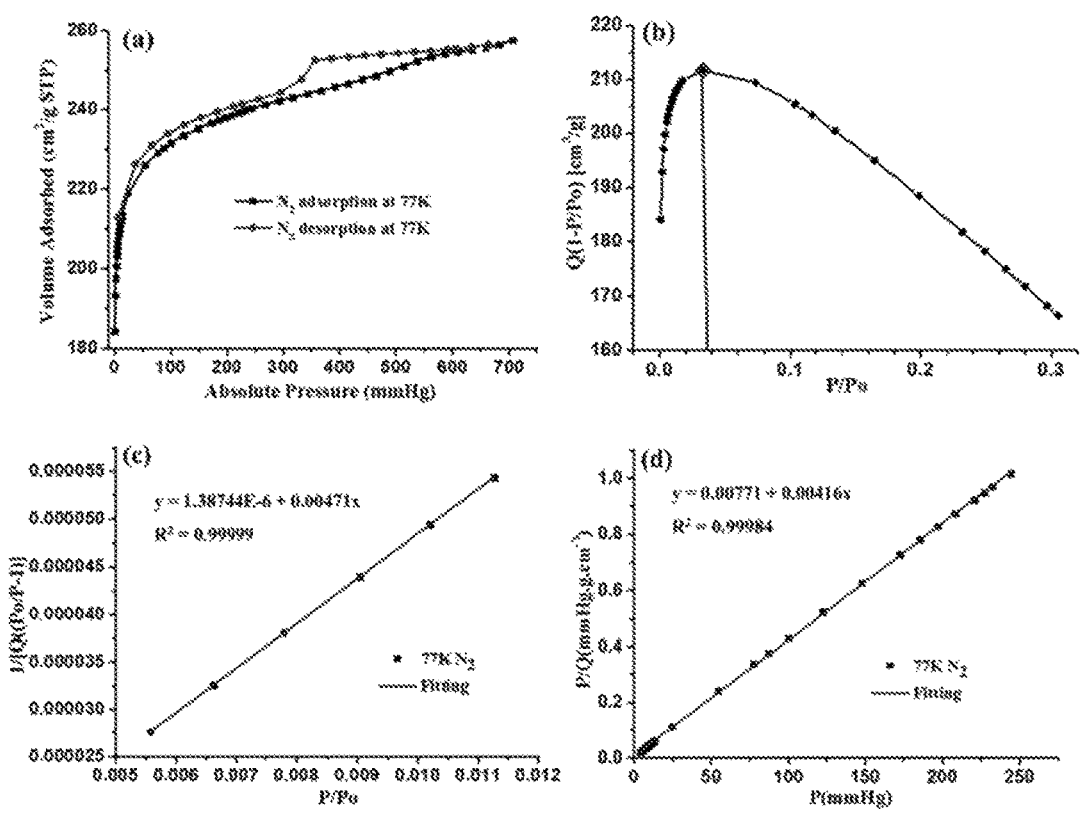
FIGS. 6A-6D show (FIG. 6A) $N_2$ sorption isotherm of UTSA-100a at 77K.

To assess the permanent porosity, the acetone-exchanged UTSA-100 was further activated under high vacuum to obtain the desolvated UTSA-100a. The porosity of UTSA-100a was evaluated by N$_2$ gas sorption at 77 K. The type I isotherm showed a sharp uptake at $P/P_0<0.1$, which clearly indicates its microporous nature (FIG. 6A). The nitrogen physisorption of UTSA-100a reached a plateau at around $P/P_0=0.1$, the saturation uptake was 257.6 cm$^3$ g$^{-1}$ and the corresponding specific pore volume was 0.399 cm$^3$ g$^{-1}$. The Langmuir (BET) surface area based on the N$_2$ adsorption isotherm at 77 K was 1098 (970) m$^2$ g$^{-1}$ for UTSA-100a, within the pressure range of $0.05<P/P_0<0.3$ (FIGS. 6B-6D).

2. Sorption of Acetylene and Ethylene within UTSA-100a

Figure 7A:
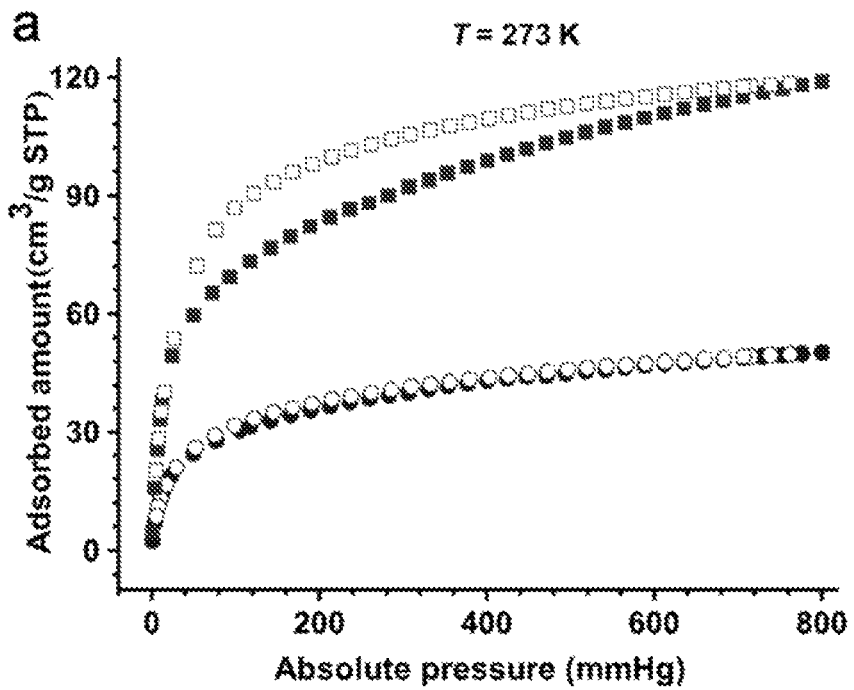
FIG. 7A & 7B show acetylene (squares) and ethylene (circles) sorption isotherms on the activated UTSA-100a at 273 K (FIG. 7A) and 296 K (FIG. 7B). Filled: adsorption; unfilled: desorption.
Figure 7B:
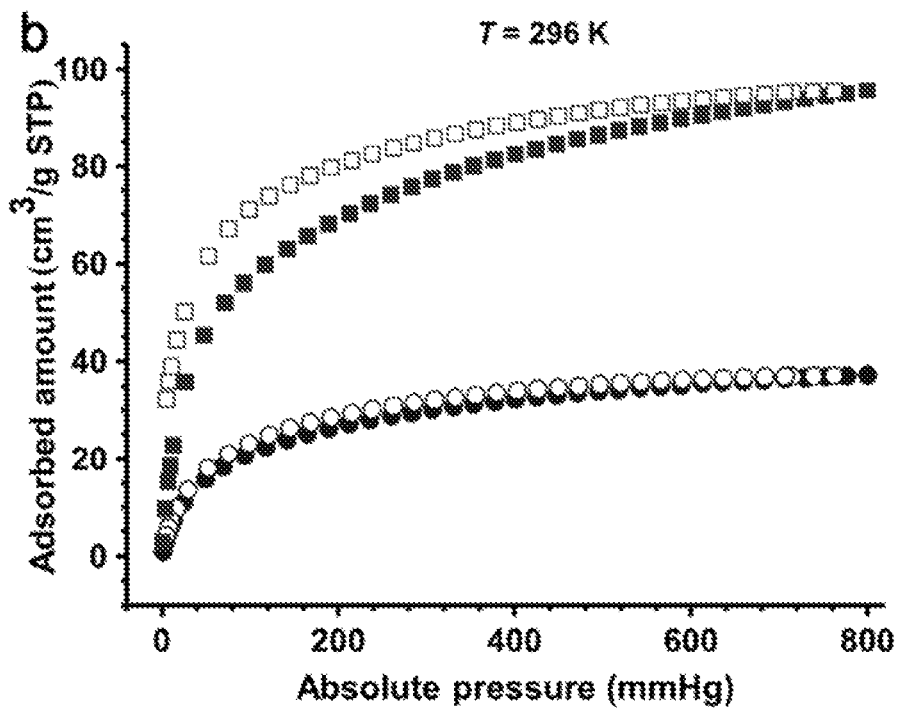

The unique pore structure encouraged examination of the capacities of UTSA-100a for the selective separation of C$_2$H$_2$/C$_2$H$_4$. The low-pressure sorption isotherms of acetylene and ethylene were collected at 273 and 296 K, respectively. At 296 K and 1 atm, the acetylene and ethylene uptake amounts of UTSA-100a were 95.6 and 37.2 cm$^3$·g$^{-1}$, respectively (FIG. 7A & 7B). As such, the acetylene uptake of UTSA-100a was moderately high while ethylene uptake was lower. As shown in Table 5, the C$_2$H$_2$/C$_2$H$_4$ uptake ratio of 2.57 in UTSA-100a was systematically higher than the examined MOFs except M'MOF-3a with narrow pores, indicating the materials potential for use in C$_2$H$_2$/C$_2$H$_4$ separations.

TABLE 5

Summary of the adsorption uptakes, selectivities and heat of adsorption data for acetylene and ethylene in M'MOF-3a, MgMOF-74, CoMOF-74, FeMOF-74, NOTT-300 and UTSA-100a at 296 K (Bloch, et al., 2012; He, et al., 2012 and Yang, et al., 2015).

|  | M'MOF-3a | MgMOF-74 | CoMOF-74 | FeMOF-74 | NOTT-300 | UTSA-100a |
|---|---|---|---|---|---|---|
| Surface area (m$^2$ g$^{-1}$) (BET) | 110 | 927 | 1,018 | 1,350 | 1370 | 970 |
| Pore volume (cm$^3$ g$^{-1}$) | 0.165 | 0.607 | 0.515 | 0.626 | 0.433 | 0.399 |
| Framework density (kg m$^{-3}$) | 1,023 | 909 | 1,169 | 1,126 | 1,062 | 1,146 |
| Size of pore window (Å) | 3.4 × 4.8 | 11 × 11 | 11 × 11 | 11 × 11 | 6.5 × 6.5 | 4.3 × 4.3 |
| C$_2$H$_2$ uptake at 1.0 bar (mmol g$^{-1}$) | 1.90 | 8.37 | 8.17 | 6.80* | 6.34** | 4.27 |
| C$_2$H$_4$ uptake at 1.0 bar (mmol g$^{-1}$) | 0.40 | 7.45 | 7.02 | 6.10* | 4.28** | 1.66 |

TABLE 5-continued

Summary of the adsorption uptakes, selectivities and heat of adsorption data
for acetylene and ethylene in M'MOF-3a, MgMOF-74, CoMOF-74, FeMOF-74, NOTT-
300 and UTSA-100a at 296 K (Bloch, et al., 2012; He, et al., 2012 and Yang, et al., 2015).

|  | M'MOF-3a | MgMOF-74 | CoMOF-74 | FeMOF-74 | NOTT-300 | UTSA-100a |
|---|---|---|---|---|---|---|
| $C_2H_2/C_2H_4$ uptake ratio | 4.75 | 1.12 | 1.16 | 1.11 | 1.48 | 2.57 |
| Selectivity for $C_2H_2/C_2H_4$[†] | 24.03 | 2.18 | 1.70 | 2.08 | 2.17 | 10.72 |
| $Q_{st}$ ($C_2H_2$) (kJ mol$^{-1}$)[‡] | 25 | 41 | 45 | 46 | 32 | 22 |

*At the temperature of 318 K.
**At the temperature of 293 K.
[†]IAST analysis for ethylene/acetylene mixtures containing 1% acetylene at 100 kPa.
[‡]$Q_{st}$ values at low surface coverage.

Figure 8:
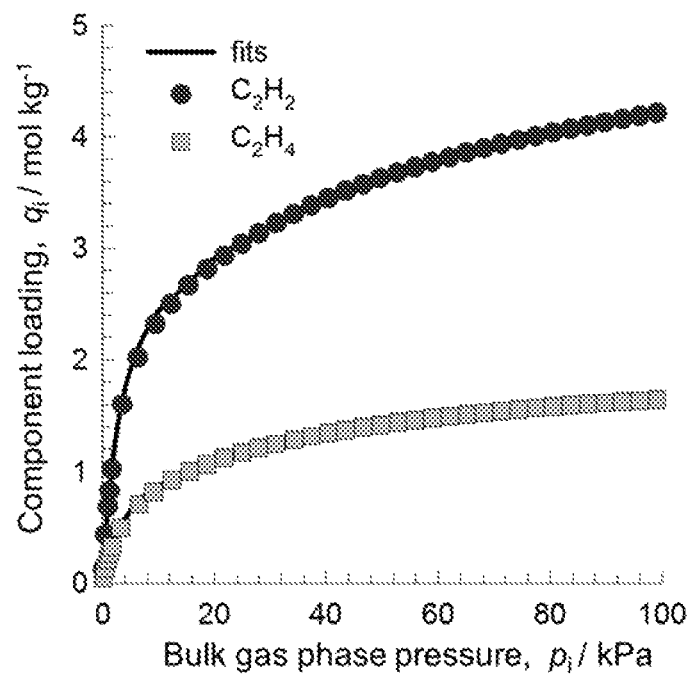
FIG. 8 shows the comparison of component loadings for $C_2H_2$ (circles) and $C_2H_4$ (squares) at 296 K in UTSA-100a with dual-Langmuir-Freundlich isotherm fits.

The measured pure component isotherm data for acetylene and ethylene on UTSA-100a were fitted with the dual-Langmuir-Freundlich isotherm model. The fitted parameter values are presented in Table 1. As illustration of the goodness of the fits, FIG. 8 presents a comparison of component loadings for acetylene and ethylene at 296 K in UTSA-100a with the isotherm fits. The fits were excellent for both components over the entire pressure range.

The binding energy of acetylene was reflected in the isosteric heat of adsorption, $Q_{st}$, defined as $$Q_{st} = RT^2 \left(\frac{\partial \ln p}{\partial T}\right)_q$$

Figure 9:
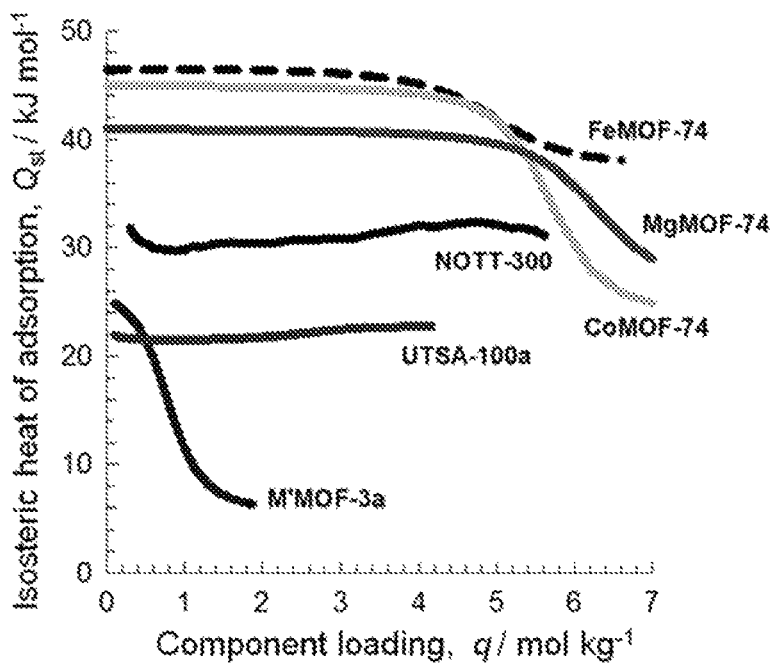
FIG. 9 shows the comparison of the heats of adsorption of $C_2H_2$ in various MOFs. The $Q_{st}$ data for NOTT-300 has been scanned from Yang, et al. (2015) for discrete points; this explains the non-smooth nature of the curve. The data for other MOFs has been taken from He, et al. (2012).

FIG. 9 presents a comparison of the heats of adsorption of acetylene in UTSA-100a with five other representative MOFs (M'MOF-3a, MgMOF-74, CoMOF-74, FeMOF-74, and NOTT-300); the calculations are based on the use of the Clausius-Clapeyron equation. The values of $Q_{st}$ in UTSA-100a and M'MOF-3a were lower than that of MOFs with coordinately unsaturated metal atoms FeMOF-74, CoMOF-74, and MgMOF-74. The value of $Q_{st}$ in UTSA-100a was also lower than for NOTT-300. This implies that the regeneration energy requirement of UTSA-100a was lower than that of FeMOF-74, CoMOF-74, MgMOF-74, and NOTT-300.

3. IAST Calculations of Adsorption Selectivities

Figures 10A, 10B, 10C:
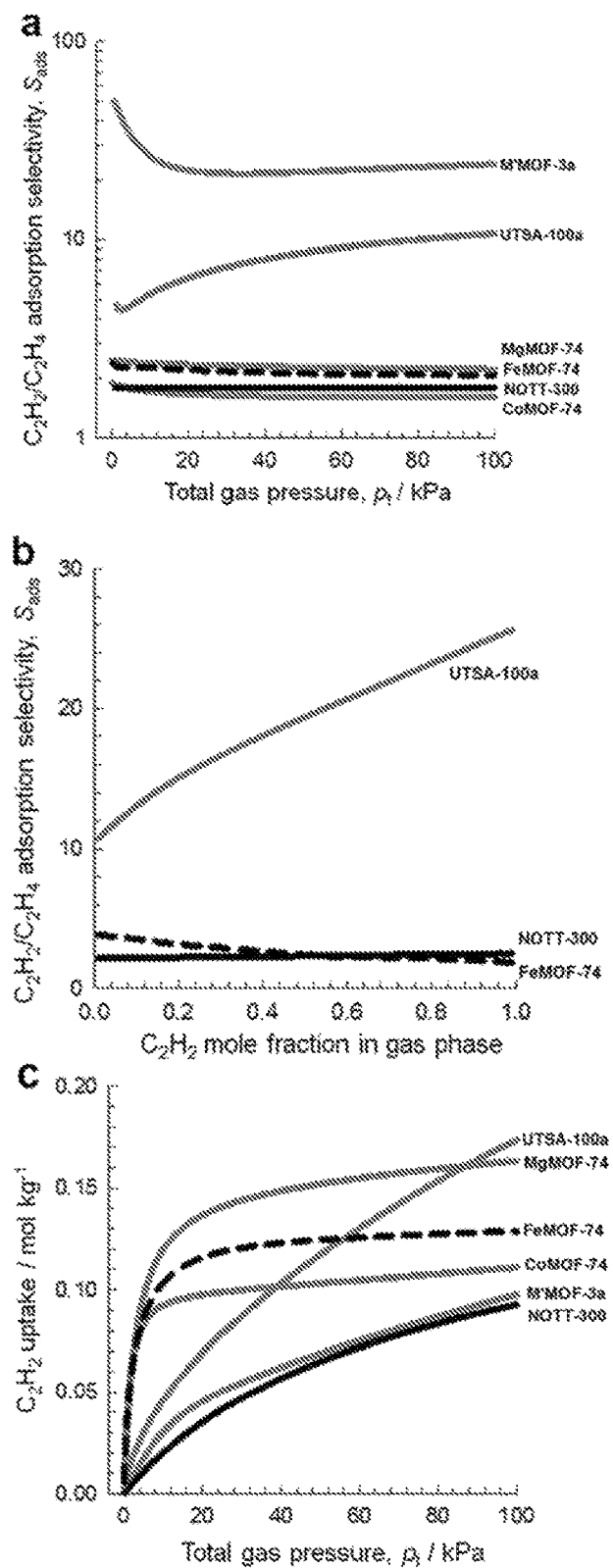
FIGS. 10A-10C show IAST calculations for binary $C_2H_2/C_2H_4$ mixture on the MOFs.

Analysis of the pure-component isotherms at 296 K via ideal adsorbed solution theory (IAST) (Myers & Prausnitz, 1965) was carried out to estimate the selectivity between acetylene and ethylene. The separation of binary acetylene/ethylene mixtures containing 1%, i.e. 10,000 ppm, of acetylene was considered. This composition is typical of industrial mixtures. FIG. 10A presents the IAST calculations of the acetylene/ethylene adsorption selectivity, defined by $$S_{ads} = \frac{q_1/q_2}{p_1/p_2}$$

The highest adsorption selectivity was with M'MOF-3a and followed by UTSA-100a. MOFs with coordinately unsaturated metal atoms MgMOF-74, CoMOF-74, and FeMOF-74 had selectivities that were in the range of 1.6 to 2.2. NOTT-300 had selectivities in the range 1.8-2.1.

In Yang, et al. (2015), the acetylene/ethylene mixtures for NOTT-300 were compared with FeMOF-74 for varying mole fraction of acetylene in the gas phase, keeping the total gas phase pressure constant at 100 kPa. In industrial practice, the compositions of acetylene in the gas phase, generally, contain less than 1%. Also, acetylene was selectively adsorbed from acetylene/ethylene mixtures, and the bulk gas phase compositions were vary from 1% at the inlet to the desired 40 ppm limit at the outlet of the fixed bed absorber. For these reasons, the selectivity calculations in the paper of Yang et al. (2015) are not representative of the conditions that are likely to be encountered in industry. Nevertheless, in order to compare out IAST calculation methodology with those of Yang et al. (2015), similar comparison, also including UTSA-100a were carried out and the results are shown in FIG. 10B. The IAST selectivity calculations for NOTT-300 and FeMOF-74 agreed reasonably well with those of Yang et al. (2015) and UTSA-100a had higher selectivity than both NOTT-300 and FeMOF-74.

As shown in FIG. 10C, the gravimetric uptake capacity of acetylene in UTSA-100a for adsorption from $C_2H_2/C_2H_4$ mixtures containing 1% $C_2H_2$ was compared with other five MOFs (M'MOF-3a, MgMOF-74, CoMOF-74, FeMOF-74, and NOTT-300). At a total gas phase pressure of 100 kPa, the hierarchy of uptake capacities for acetylene was UTSA-100a>MgMOF-74>FeMOF-74>CoMOF-74>M'MOF-3a≈NOTT-300.

4. Acetylene/Ethylene Breakthrough Simulations and Experiments

Figures 11A, 11B, 11C, 11D:
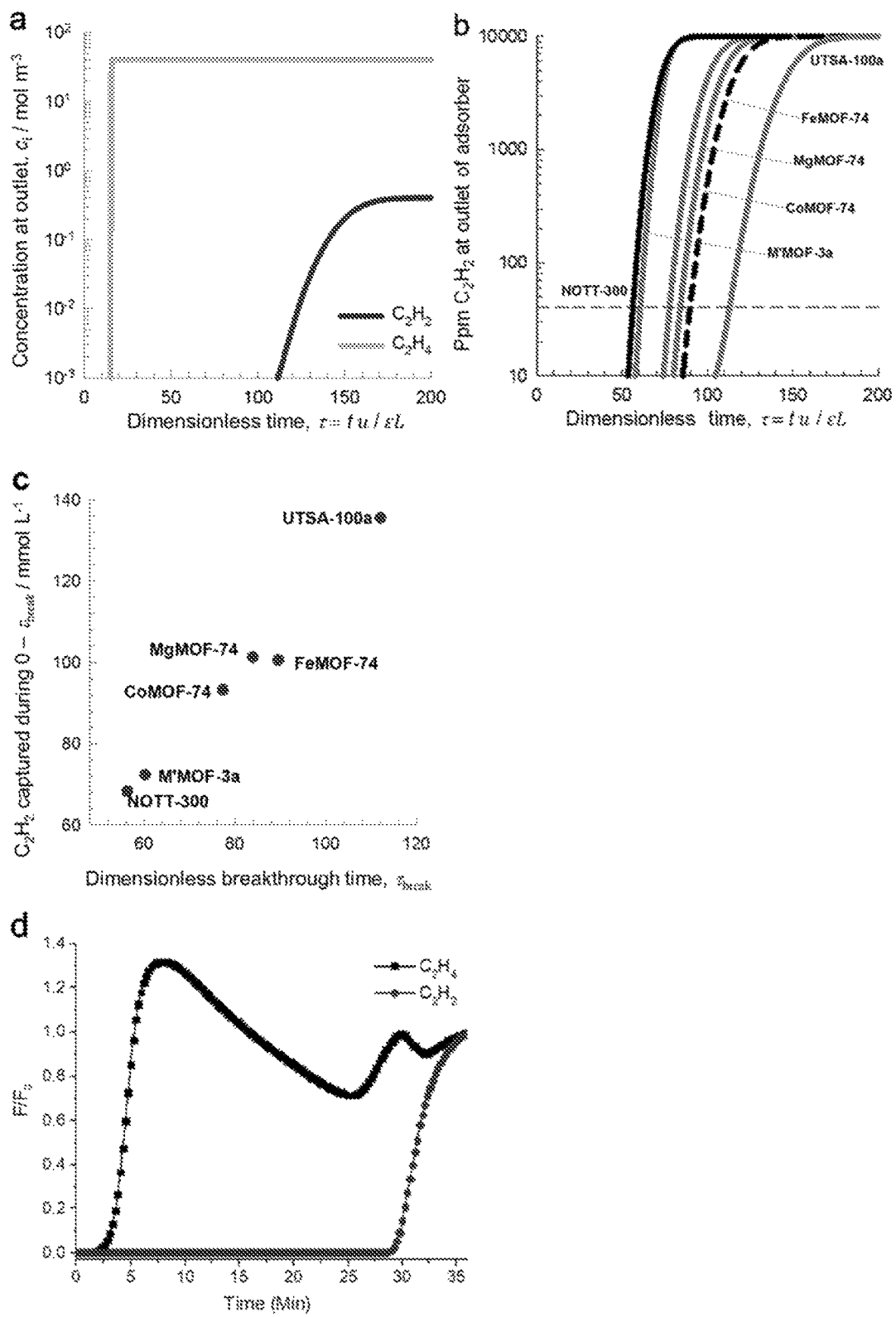
FIGS. 11A-11D show simulative and experimental column breakthrough experiments for $C_2H_2/C_2H_4$ mixture containing 1% $C_2H_2$ at 296 K and 100 kPa.

Breakthrough simulations were carried out for the $C_2H_2/C_2H_4$ (1:99, v/v) mixture, which composition is typical of industrial mixtures, in a fixed bed to demonstrate the feasibility of purification of ethylene in a Pressure Swing Adsorption (PSA) operation. The transient breakthrough simulations showed the concentrations of $C_2H_2/C_2H_4$ exiting the adsorber packed with UTSA-100a as a function of the dimensionless time, τ (FIG. 11A). Analogous breakthrough simulations were performed for M'MOF-3a, MgMOF-74, CoMOF-74, FeMOF-74, and NOTT-300. On the basis of the gas phase concentrations, the impurity level of acetylene in the gas mixture exiting the fixed bed packed with six different MOFs was calculated. FIG. 11B shows the ppm $C_2H_2$ in the outlet gas mixture exiting an adsorber packed with M'MOF-3a, MgMOF-74, CoMOF-74, FeMOF-74, NOTT-300 and UTSA-100a. At a certain time, $\tau_{break}$, the impurity level exceeded the desired purity level of 40 ppm (indicated by the dashed line), that corresponds to the purity requirement of the feed to the polymerization reactor. The adsorption cycle needed to be terminated at that time $\tau_{break}$ and the regeneration process needed to be initiated. From a material balance on the adsorber, the amount of acetylene captured during the time interval $0-\tau_{break}$ was be determined. The amount of acetylene captured in UTSA-100a during the time $0-\tau_{break}$ was 137.6 mmol/L, which is the longest time interval among the compared six MOFs and approximately twice that of NOTT-300 (Table 6). A plot of the amount of acetylene captured plotted as a function of the time interval $\tau_{break}$ is presented in FIG. 11C. The hierarchy of acetylene capture capacities was UTSA-100a>MgMOF-74>FeMOF-74>CoMOF-74>M'MOF-3a>NOTT-300. The significantly superior performance of UTSA-100a was attributable to a combination of high adsorption selectivity and high uptake capacity. M'MOF-3a had the highest selectivity but the lowest uptake capacity resulting in poorer performance in the industrial fixed bed adsorber.

TABLE 6

Breakthrough calculations for separation of C2H2/C2H4 mixture containing 1 mol % C2H2 at 296 K. The data for FeMOF-74 is at a temperature of 318 K; this is the lowest temperature used in the isotherm measurements of Bloch, et al. (2012) The data for NOTT-300 is at 293 K, for which the isotherm data is available in Yang, et al. (2015) The product gas stream contains less than 40 ppm C2H2.

|  | Dimensionless Breakthrough Time, $\tau_{break}$ | Adsorbed Amount of $C_2H_2$ during $0-\tau_{break}$, mmol $L^{-1}$ |
|---|---|---|
| UTSA-100a | 113.7 | 137.6 |
| MgMOF-74 | 84.0 | 101.3 |
| FeMOF-74 | 89.0 | 100.7 |
| CoMOF-74 | 77.4 | 93.3 |
| M'MOF3a | 60.2 | 72.3 |
| NOTT-300 | 56.3 | 68.3 |

To evaluate the performance of UTSA-100a in the actual adsorption-based separation and purification processes, breakthrough experiments were performed in which an $C_2H_2/C_2H_4$ (1:99, v/v) mixture was flowed over a packed bed of UTSA-100a solid with a total flow of 2 mL/min at 296 K. As shown in FIG. 11D, the separation of $C_2H_2/C_2H_4$ (1:99, v/v) mixture through the column packed bed of UTSA-100a solid was efficiently achieved.

5. Pore Structure Analysis and Molecular Simulation Studies

Figures 12A, 12B, 12C, 12D:
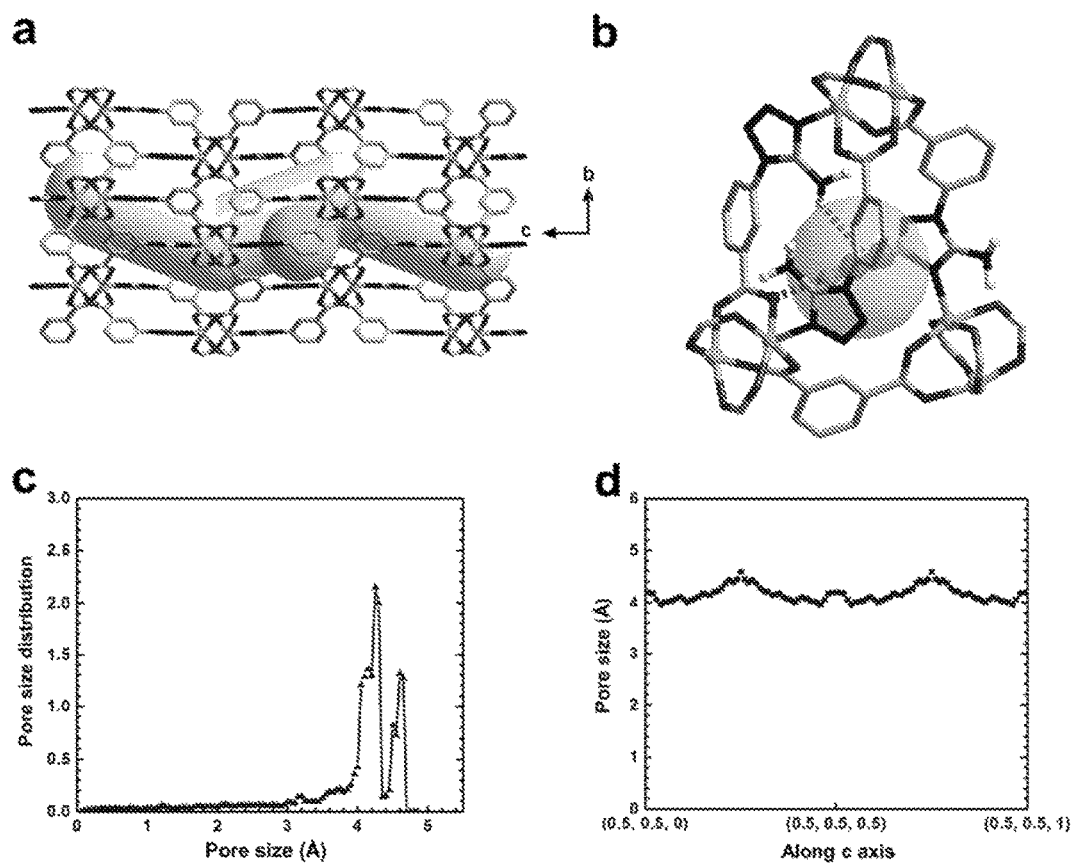
FIGS. 12A-12D show the pore structure of UTSA-100, the $C_2H_2$ binding site within the framework, and pore size distributions.

The pore structure of UTSA-100 can be viewed as 1D channel-like ones along c axis of the crystal. Adjacent channels were interconnected through narrow cages (with 3.3 Å openings). The overall MOF pore size was centered at 4.3 Å, with rather narrow distribution (FIG. 12C). Without wishing to be bound by any theory, gas adsorption and diffusion would thus take place predominantly within individual channel pores, with inter-channel diffusion limited by the narrow window opening between adjacent channels and the size of gas molecules. The pore size variation along the pore channel (in crystallography c axis direction) is shown in FIG. 5d. Clearly, the pore limiting size (for the access of guest gas molecule into the MOF crystal) was 3.96 Å, while the largest cavity within the channel was 4.6 Å in diameter. Note that the empirical kinetic diameters of $C_2H_2/C_2H_4$ were ~3.3/4.2 (3.32×3.34×5.70 Å$^3$ for $C_2H_2$ vs 3.28×4.18×4.84 Å$^3$ for $C_2H_4$), respectively (Breck, 1974; Sircar & Myers, 2003; Li, et al., 2009 and Aguado et al., 2012). For ethylene, its kinetic diameter was slightly larger than the channel pore opening of UTSA-100a, and much larger than the inter-channel window size. These two factors may hinder or block the ethylene adsorption and diffusion in the MOF structure, leading to the much lower ethylene uptakes than acetylene ones.

To further understand the acetylene adsorption in UTSA-100a, detailed computational investigations were performed. The bare UTSA-100a structure was first optimized by first-principles DFT-D (dispersion-corrected density-functional theory) calculations, where van der Waals (vdW) interactions were corrected by empirical $r^{-6}$ terms (Giannozzi, et al., 2009). The optimized structure is fairly close to the experimentally determined structure. Then acetylene molecules were introduced to various locations of the channel pore, and further optimized the "UTSA-100a+$C_2H_2$" structures using DFT-D. Interestingly, the guest acetylene molecules all get relaxed to a particular adsorption sites. In FIG. 12B, this preferred acetylene adsorption location is plotted. The acetylene sits right at the small cage connecting two adjacent channel pores. The relatively strong binding clearly comes from multiple-point interactions of the molecule with framework (particularly, the metal center O and the linker —$NH_2$ groups, FIG. 12B). It is suggested that the relatively narrower pore size allows and reinforces one acetylene molecule to interact mutually with —$NH_2$ group and one metal center O atom. The adsorbed acetylene is slightly distorted with an induced dipole moment. The H—C—C bond angle of acetylene is 178.8°, comparable to that of acetylene adsorbed on the open-Cu site in HKUST-1 (~178°) (Xiang, et al., 2009). The static acetylene binding energy, derived from the DFT-D calculation, is ~31.3 kJ/mol, which are somewhat larger than the experimental $Q_{st}$ value but still reasonable, considering the accuracy limitation of the DFT-D approach.

Example 4

Discussion

Removal of acetylene from acetylene/ethylene mixtures containing 1% acetylene is a challenging industrial separation task. To evaluate a porous material for acetylene removal from ethylene, adsorption selectivity and saturation uptake capacity have been deemed as two useful criteria, and high values for both of them are needed to achieve high effectiveness and high efficiency for acetylene removal. However, which factor plays the dominant role depends on the composition of gas mixtures. For the acetylene/ethylene mixtures containing 1% acetylene, without wishing to be bound by any theory, adsorption selectivity is more important than acetylene adsorption capacity. Comparing to other five well-known MOFs (M'MOF-3a, MgMOF-74, CoMOF-74, FeMOF-74, and NOTT-300), the improved performance of UTSA-100a in removing acetylene from acetylene/ethylene mixtures containing 1% acetylene is attributable to the collaboration of high adsorption selectivity and high uptake capacity at ambient conditions. From the structure point of view, UTSA-100a has suitable pores and opening windows to enforce its high sieving effects and thus high adsorption selectivities, while the suitable cages and immobilized functional sites such —$NH_2$ further maximize the acetylene uptakes.

Figure 13:
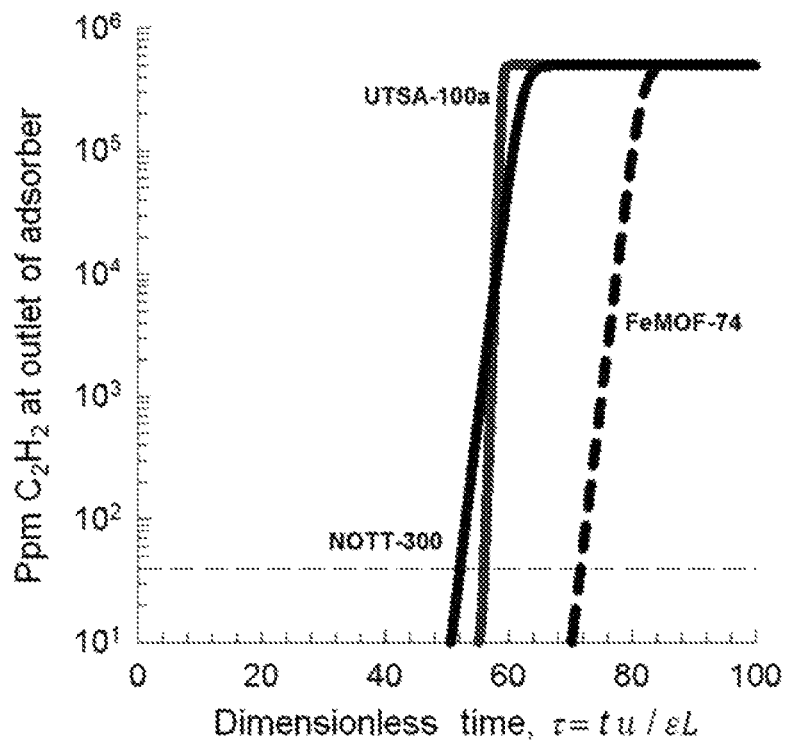
FIG. 13 shows the comparison of breakthroughs for UTSA-100a (dark gray solid line), NOTT-300 (black solid line), and FeMOF-74 (black dashed line) for 50:50 acetylene/ethylene mixtures at 296 K and 100 kPa.
Figure 14:
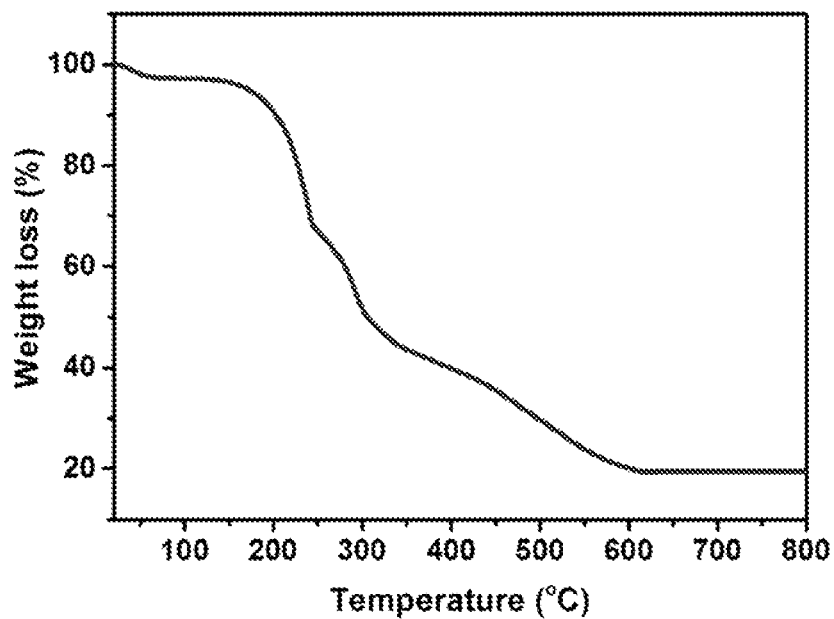
FIG. 14 shows a TGA curve of UTSA-100.

The comparisons of different MOFs with acetylene/ethylene mixtures containing 1% acetylene are useful as the comparison utilizes representative of industrial compositions. If the performance of UTSA-100a, NOTT-300, and FeMOF-74 for 50/50 acetylene/ethylene mixtures were compared, the conclusions were different because in this case, capacity considerations should be considered. FIG. 13 presents a comparison of breakthroughs for UTSA-100a, NOTT-300, and FeMOF-74 for 50/50 acetylene/ethylene mixtures. In this case the performance of NOTT-300 and UTSA-100a were nearly the same. Improved separations were achieved with FeMOF-74 as that MOF has a high capacity to adsorb acetylene. These results also underscored the need for a proper evaluation of MOFs using transient breakthroughs. Comparisons based purely on selectivities may lead to the wrong conclusions.

\* \* \*

All of the compounds, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the invention. All variations and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

Aguado et al., *J. Am. Chem. Soc.* 134, 14635-14637, 2012.
An et al., *Nat. Commun.* 3, 604, 2012.
Bhattacharya & Gubbins, *Langmuir* 22, 7726-7731, 2006.
Bloch et al., *Science* 335, 1606-1610, 2012.
Breck, W. Zeolite Molecular Sieves: Structure, Chemistry and Use (John Wiley & Sons, Inc., 1974).
Burd et al., *J. Am. Chem. Soc.* 134, 3663-3666, 2012.
Chen et al., *Acc. Chem. Res.* 43, 1115-1124, 2010.
Chen et al., *Angew. Chem. Int. Ed.* 45, 1390-1393, 2006.
Das, et al., *J. Am. Chem. Soc.* 134, 8703-8710, 2012.
Farha et a., *Nat. Chem.* 2, 944-948, 2010.
Férey et al., *Science* 309, 2040-2042, 2005.
Furukawa et al., *Science,* 341, 1230444, 2013.
Giannozzi et al., *J. Phys.: Condens. Matter* 21, 395502, 2009.
Guo et al. *Angew. Chem. Int. Ed.* 50, 3178-3181, 2011.
He et al., *Chem. Commun.* 48, 11813-11831; 2012.
He et al., *Energy Environ. Sci.* 5, 9107-9120, 2012.
Krishna & Long, *J. Phys. Chem. C* 115, 12941-12950, 2011.
Krishna, *Microporous Mesoporous Mater.* 185, 30-50, 2014.
Krishna, *Phys. Chem. Chem. Phys.* 17, 39-59, 2015.
Lan et al., *Adv. Mater.* 23, 5015-5020, 2011.
Lewis, U.S. Pat. No. 3,837,144, 1974.
Li et al., *Angew. Chem. Int. Ed.* 51, 1412-1415; 2012.
Li et al., *Chem. Soc. Rev.* 38, 1477-1504, 2009.
Li et al., *J. Am. Chem. Soc.* 136, 1202-1205, 2014).
Li et al., *J. Am. Chem. Soc.* 136, 6207-6210, 2014.
Li et al., *J. Phys. Chem. Lett.* 5, 3468-3479, 2014.
Li et al., *Nat. Commun.* 4, 1538, 2013.
Lin et al., *J. Am. Chem. Soc.* 134, 784-787, 2012.
Ma et al., *J. Am. Chem. Soc.* 131, 4610-4612, 2009.
Mohideen et al., *Nat. Chem.* 3, 304-310, 2011.
Molero et al., *J. Catal.,* 181, 49-56, 1999.
Motkuri et al., *Nat. Commun.* 5, 4368, 2014.
Myers & Prausnitz, *AIChE J.* 11, 121-130, 1965.
Nugent et al., *Nature* 495, 80-84, 2013.
Sato et al., *Science* 343, 167-170, 2014.
Shekhah et al., *Nat. Commun.* 5, 4228, 2014.
Sheldrick, G. M. Program for Structure Refinement. Germany, 1997.
Sircar & Myers, Gas Separation by Zeolites. In Handbook of Zeolite Science and Technology, Marcel Dekker Inc., 2003.
Spek, *A Multipurpose Crystallographic Tool* (Utrecht University, 2001).
Spek, A. L. PLATON: The University of Utrecht: Utrecht, The Netherlands, 1999.
Spek, PLATON. *J. Appl. Crystallogr.* 36, 7-13, 2003.
Studt et al., *Science* 320, 1320-1322, 2008.
Sundaram et al., *Kirk-Othmer Encyclopedia of Chemical Technology,* 4th edn, 877-915, 1995.
Vaidhyanathan et al., *Science* 330, 650-653, 2010.
Voitekhovich et al., *Chem. Heterocycl. Compd.* 41, 999-1004, 2005.
Wen et al., *Chem. Commun.* 51, DOI: 10.1039/C4CC09999K, 2015.
Xiang et al., *Angew. Chem. Int. Ed.* 49, 4615-4618, 2010.
Xiang et al., *J. Am. Chem. Soc.* 131, 12415-12419, 2009.
Xiang et al., *Nat. Commun.* 2, 204; 2011.
Xiang et al., *Nat. Commun.* 3, 954; 2012.
Yang et al., *Nat. Chem.* 7, 121-129, 2015.
Zhang & Chen, *J. Am. Chem. Soc.* 131, 5516-5521, 2009.
Zhang et al., *Nat. Commun.* 3, 642, 2012.
Zhao et al., *Nat. Commun.* 4, 2344, 2013).
Zhao et al., *Science* 306, 1012-1015, 2004.

What is claimed is:

1. A metal-organic framework (MOF) comprising a repeat unit of the formula [ML], wherein L is a ligand of the formula:

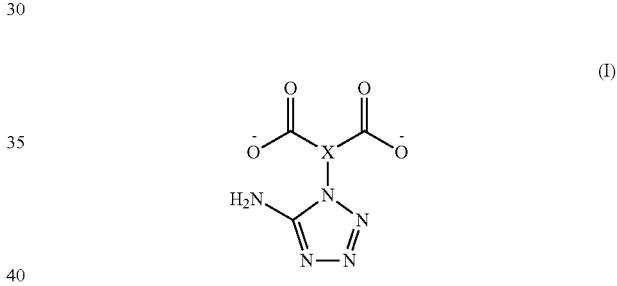

wherein:
X is an arenetriyl$_{(C \leq 12)}$, a heteroarenetriyl$_{(C \leq 12)}$, or a substituted version of either of these groups; and
M is a divalent transition metal cation.

2. The MOF of claim 1, wherein M is divalent copper ion.

3. The MOF of claim 1, wherein L is a ligand of the formula:

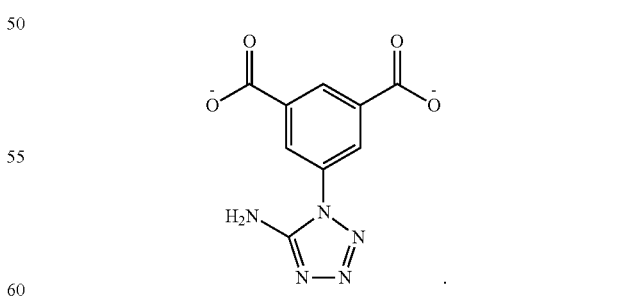

4. The MOF of claim 1, further comprising one or more than one type of guest molecule.

5. The MOF of claim 4, wherein one type of guest molecule is a solvent molecule.

6. The MOF of claim 5, wherein the solvent molecule is water, N,N'-dimethylformamide, methanol, or acetone.

7. The MOF of claim 4, wherein one type of guest molecule is a gas molecule.

8. The MOF of claim 7, wherein the gas molecule is an alkyne$_{(C \leq 8)}$.

9. The MOF of claim 7; wherein the gas molecule is an alkene$_{(C \leq 8)}$.

10. The MOF of claim 7, wherein the guest molecule is a mixture of acetylene and ethylene.

11. The MOF of claim 1, wherein the MOF is substantially free from any solvent molecules.

12. The MOF of claim 1, wherein the MOF has a weight percentage at least 90% attributable to repeat units of the formula [ML].

13. The MOF of claim 1, wherein the MOF has been adhered to a fixed surface.

14. A metal-organic framework (MOF) comprising a repeat unit of the formula [CuL], wherein L is a ligand of the formula:

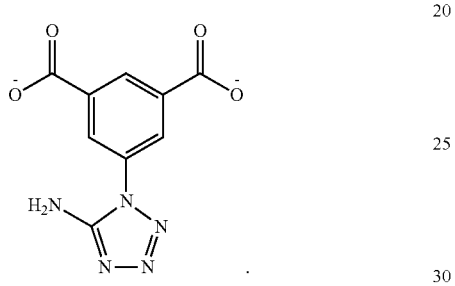

* * * * *